(12) United States Patent
DiMagno

(10) Patent No.: US 11,214,820 B2
(45) Date of Patent: Jan. 4, 2022

(54) FUNCTIONALLY MODIFIED POLYPEPTIDES AND RADIOBIOSYNTHESIS

(71) Applicant: Ikaria Inc., Cambridge, MA (US)

(72) Inventor: Stephen DiMagno, Chicago, IL (US)

(73) Assignee: Ikaria Inc., Cambridge, MA (US)

( * ) Notice: Subject to any disclaimer, the term of this patent is extended or adjusted under 35 U.S.C. 154(b) by 576 days.

(21) Appl. No.: 15/695,831

(22) Filed: Sep. 5, 2017

(65) Prior Publication Data

US 2018/0066298 A1    Mar. 8, 2018

Related U.S. Application Data

(60) Provisional application No. 62/383,382, filed on Sep. 2, 2016.

(51) Int. Cl.

| | |
|---|---|
| *C12P 21/02* | (2006.01) |
| *C07C 327/44* | (2006.01) |
| *C07C 233/51* | (2006.01) |
| *C07K 14/545* | (2006.01) |
| *C07B 59/00* | (2006.01) |
| *C07C 327/42* | (2006.01) |
| *C07K 14/54* | (2006.01) |
| *C12N 9/00* | (2006.01) |

(52) U.S. Cl.
CPC .......... *C12P 21/02* (2013.01); *C07B 59/001* (2013.01); *C07B 59/008* (2013.01); *C07C 233/51* (2013.01); *C07C 327/42* (2013.01); *C07C 327/44* (2013.01); *C07K 14/54* (2013.01); *C07K 14/545* (2013.01); *C12N 9/93* (2013.01); *C12Y 601/01026* (2013.01); *C07B 2200/05* (2013.01)

(58) Field of Classification Search
CPC ....................................................... C12P 21/02
See application file for complete search history.

(56) References Cited

U.S. PATENT DOCUMENTS

| | | |
|---|---|---|
| 2013/0183761 A1 | 7/2013 | Chin et al. |
| 2018/0066298 A1 | 3/2018 | Dimagno |

OTHER PUBLICATIONS

Lim, S et al. (Jun. 10, 2015) Site-specific Albumination of a Therapeutic Protein with Multi-subunit to Prolong Activity In Vivo. J. Control Release, 207:93-100.
PubChem CID 2755858, [CAS 56656-34-9] (Jul. 19, 2005, retrieved Mar. 16, 2018). https://pubchem.ncbi.nlm.nih.gov/compound/2755858#section=Top] pp. 4.

*Primary Examiner* — Amber D Steele
(74) *Attorney, Agent, or Firm* — Lathrop GPM LLP; Giulio DeConti; Michael Spellberg

(57) ABSTRACT

Provided herein are compositions and methods for generating polypeptides using non-natural amino acids (nnAAs) and genetic machinery, wherein the modified polypeptides, such as therapeutic polypeptides, bind to albumin, such as serum albumin. Methods of substituting a non-natural amino acid in a first polypeptide to obtain a modified polypeptide, the nnAA in some instances comprising an albumin targeting group, are disclosed, as are methods for making populations of such modified polypeptides. A therapeutic polypeptide, interleukin-1 receptor antagonist (IL-1RA) is exemplified using the disclosed methods.

6 Claims, 4 Drawing Sheets n = 1, 2

FUNCTIONALLY MODIFIED POLYPEPTIDES AND RADIOBIOSYNTHESIS

RELATED APPLICATIONS

This patent application claims the benefit of U.S. Provisional Patent Application No. 62/383,382, filed Sep. 2, 2016, which is incorporated herein by reference in its entirety.

TECHNICAL FIELD

The invention is directed to the field of protein drugs. Specifically, the invention is directed to improving the pharmacokinetics of protein drugs through the incorporation of non-natural amino acids into therapeutic polypeptides using genetic machinery.

BACKGROUND

More than one hundred therapeutic proteins are used currently to treat cancer, immune diseases, and diabetes, among other disorders, and hundreds more are in clinical trials (Dimitrov D S. Therapeutic Proteins. In: Therapeutic Proteins: Methods and Protocols, Methods in Molecular Biology, Editor: Voynov V, Caravella J A. Springer Science+Business Media; 2012. p. 1-26). Antibodies comprise half of the market of currently prescribed therapeutic peptides. In part, the utility of antibodies derives from their relatively long serum half-lives compared to other peptides and proteins, which are generally cleared and/or metabolized quickly. Such rapid clearance often dictates aggressive dosing schedules for non-antibody therapeutic proteins, which can increase the risk of side effects, shrink the therapeutic window, and have a negative impact upon patient compliance. For example, Kineret® (anakinra), a 17 kD therapeutic protein currently prescribed for the treatment of rheumatoid arthritis, is administered by daily subcutaneous injection (70-100 mg, 1-2 mg/kg) over several months. Peak anakinra serum concentrations occur at ~6 h after injection.

Several strategies are currently employed to extend the serum lifetime of therapeutic peptides and proteins (Pollaro L, Heinis C. Strategies to prolong the plasma residence time of peptide drugs. *MedChemComm.* 2010; 1, 319-24), including alteration of peptide sequence and secondary structure to minimize protease activity (Timmerman P et al. Functional reconstruction and synthetic mimicry of a conformational epitope using CLIPS™ technology. *J Mol Recognit.* 2007; 20, 283-99; Houston M E et al. Lactam Bridge Stabilization of α-Helices: The Role of Hydrophobicity in Controlling Dimeric versus Monomeric α-Helices. *Biochemistry (Mosc).* 1996; 35, 10041-50; Sim S, et al. Directional Assembly of α-Helical Peptides Induced by Cyclization. *J Am Chem Soc.* 2012; 134, 20270-2) and PEGylation (Veronese F M. Peptide and protein PEGylation: a review of problems and solutions. *Biomaterials.* 2001; 22, 405-17; Jevševar S, et al. PEGylation of therapeutic proteins. *Biotechnology Journal.* 2010; 5, 113-28; Greenwald R B, et al. Effective drug delivery by PEGylated drug conjugates. *Advanced Drug Delivery Reviews.* 2003; 55, 217-50; Xue X, et al Phenyl Linker-Induced Dense PEG Conformation Improves the Efficacy of C-Terminally MonoPEGylated Staphylokinase. *Biomacromolecules.* 2013; 14, 331-41) to limit globular filtration. A more promising, and potentially generalizable, approach is to introduce human serum albumin (HSA) targeting elements into the protein (Kratz F. Albumin as a drug carrier: Design of prodrugs, drug conjugates and nanoparticles. *J Controlled Release.* 2008; 132, 171-83; Dennis M S, et al. Albumin Binding as a General Strategy for Improving the Pharmacokinetics of Proteins. *J Biol Chem.* 2002; 277, 35035-43). Albumin targeting is currently accomplished either by genetic engineering or post-translational bioconjugation strategies. Genetically encoded albumin-targeting peptides (AlbudAb™ (O'Connor-Semmes R L, et al. GSK2374697, a Novel Albumin-Binding Domain Antibody (AlbudAb), Extends Systemic Exposure of Exendin-4: First Study in Humans-PK/PD and Safety. *Clin Pharmacol Ther* (N Y, N.Y., U S). 2014; 96, 704-12; WO2010108937A2; Holt Li, et al. Anti-serum albumin domain antibodies for extending the half-lives of short lived drugs. *Protein Eng, Des Sel.* 2008; 21, 283-8; Holt U, et al. Domain antibodies: proteins for therapy. *Trends Biotechnol.* 2003; 21, 484-90) and others (Dennis, 2002, supra; Langenheim J F, Chen W Y. Improving the pharmacokinetics/pharmacodynamics of prolactin, GH, and their antagonists by fusion to a synthetic albumin-binding peptide. *J Endocrinol.* 2009; 203, 375-87) can be incorporated in a highly controlled fashion to extend the serum lifetime of therapeutic peptides, but this improvement in pharmacokinetic properties (PK) comes at the cost of a relatively large perturbation to the native protein structure. In contrast, post-translational modification of proteins can introduce relatively small albumin targeting molecules, but this approach can yield heterogeneous mixtures that are often difficult to characterize fully, and include macromolecular species with potentially widely varying PK and target affinity.

Significant progress toward the control of post-translational modification is possible with the introduction of genetically encoded "clickable" amino acids (Kurra Y, et al. Two Rapid Catalyst-Free Click Reactions for In Vivo Protein Labeling of Genetically Encoded Strained Alkene/Alkyne Functionalities. *Bioconjugate Chem.* 2014; 25, 1730-8; Milles S, et al. Click Strategies for Single-Molecule Protein Fluorescence. *J Am Chem Soc.* 2012; 134, 5187-95; Hertweck C. Biosynthesis and Charging of Pyrrolysine, the 22nd Genetically Encoded Amino Acid. *Angew Chem, Int Ed.* 2011; 50, 9540-1; Plass T, et al. Genetically Encoded Copper-Free Click Chemistry. *Angew Chem, Int Ed.* 2011; 50, 3878-81, S/1-S/13; Nguyen D P, et al. Genetic encoding and labeling of aliphatic azides and alkynes in recombinant proteins via a pyrrolysyl-tRNA Synthetase/tRNA(CUA) pair and click chemistry. *J Am Chem Soc.* 2009; 131, 8720-1), but this approach has inherent weaknesses for therapeutic protein development: the chemistry used to "click" on the albumin targeting group needs to be extremely efficient, and methods are required to separate the functionalized protein from those featuring unreacted or partially degraded side chains. Despite vast improvements in bioconjugation using click chemistry, generalizable reagents and reactions conditions required to meet these criteria are still lacking (Reddington S C, et al. Residue choice defines efficiency and influence of bioorthogonal protein modification via genetically encoded strain promoted Click chemistry. *Chem Commun* (Cambridge, U K). 2012; 48, 8419-21).

An ideal solution to the albumin-targeting problem for therapeutic proteins would maintain the control of the genetic approach, cause a minimal structural perturbation characteristic of a small molecule albumin targeting tag, and not require any post-translational protein modification.

SUMMARY OF INVENTION

In a first aspect, disclosed herein are methods of substituting a natural amino acid in a first polypeptide with a non-natural amino acid to obtain a modified polypeptide, wherein the non-natural amino acid comprises a moiety selected from the group consisting of: an albumin-targeting group, a radiolabel, and a radiolabelled albumin-targeting group, comprising:
(a) selecting at least one amino acid residue in the first polypeptide to be substituted with the non-natural amino acid;
(b) selecting a polynucleotide encoding the first polypeptide;
(c) modifying the polynucleotide such that the amino acid residue to be substituted is encoded by a nonsense codon;
(d) expressing the modified polynucleotide in a cell, wherein the cell is in the presence of the non-natural amino acid and expresses a suppressor tRNA and its cognate tRNA synthetase wherein the suppressor tRNA recognizes the nonsense codon of step (c), and the cell incorporates the non-natural amino acid into the modified polypeptide at the nonsense codon of step (c) during translation. Optionally, a further purifying step (e) can be included. In such aspect, the non-natural amino acid can be represented by the formula:

A-T wherein A is an amino acid selected from the group consisting of lysine, ornithine, arginine, serine, threonine, asparagine and glutamine, and T is a moiety selected from the group consisting of: an albumin-targeting group, a radiolabel, and a radiolabelled albumin-targeting group. In one embodiment, T is an albumin targeting group. In an embodiment, the albumin targeting group is selected from the group consisting of:

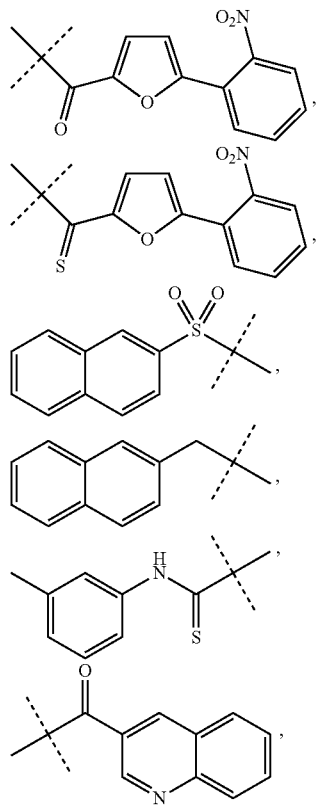

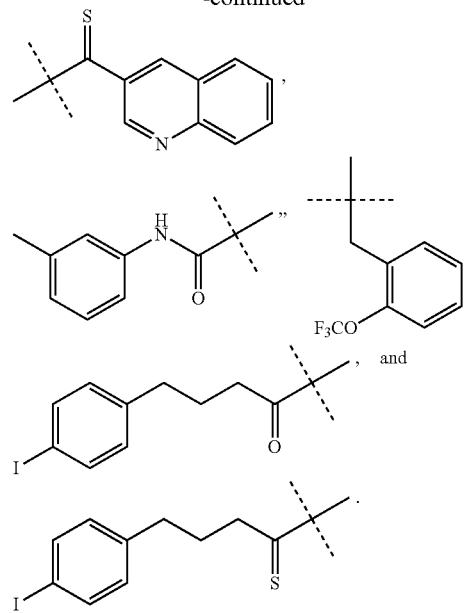

In another embodiment, the albumin targeting group comprises an aryl or heteroaryl moiety and a thioyl moiety, such that A-T comprises a thioamide moiety. In a particular embodiment, the thioyl moiety is conjugated to the aryl or heteroaryl moiety.

The non-natural amino acid can be Nε-(4-(4-iodophenyl)butanoyl)lysine, NE-(4-(4-iodophenyl)butanethioyl)lysine, or pharmaceutically acceptable salts thereof. The non-natural amino acid can comprise a radiolabelled albumin-targeting group. The non-natural amino acid can comprise a radiolabel. The nonsense codon can be an amber, opal, or ochre nonsense codon. The non-natural amino acid can be radiolabelled, such as with $^{123}$I, $^{124}$I, $^{125}$I or $^{131}$I. The suppressor tRNA can be tRNA$_{CUA}^{Pyl}$ with its cognate tRNA synthetase can be pyrrolysyl-tRNA synthetase. The cell can be radiation resistant. The cell can be a bacterial cell, a fungal cell, a plant cell, or a mammalian cell, such as a bacterial *Escherichia coli* cell or a fungal *Saccharomyces cerevisiae* cell. In the case of a radiation-resistant bacterial cell, the RecA, YfjK, and DnaB proteins in the cell can be mutated (comprising the mutations for each protein RecA (D276N); YfjK (A151D); and DnaB (P80H)); and in the case of a radiation-resistant *E. coli* cell can be derived from *E. coli* strain C321.ΔA. In the case where the cell is a bacterial cell, the cell can comprise only nonsense codons that are not the nonsense codon present in the polynucleotide and/or does not express factors that decode the nonsense codon present in the polynucleotide; for example, the nonsense codon present in the nucleotide is an amber nonsense codon, and the factor is release factor-1. In this first aspect, the first polypeptide can be a therapeutic polypeptide, such as one selected from the group consisting of anticoagulants, blood factors, bone morphogenetic proteins, engineered protein scaffolds, enzymes, growth factors, hormones, interferons, interleukins, and thrombolytics. Alternatively, the therapeutic polypeptide is an antigen-binding polypeptide, such as one selected from the group consisting of an antibody, a chimeric antibody, a monoclonal antibody, a single chain antibody, Fab, Fab', F(ab')$_2$, Fv, and scF. The therapeutic polypeptide can be an Fc fusion. The therapeutic polypeptide can be an interleukin-1 receptor antagonist. In this first aspect, the modified polypeptide can have enhanced binding to human serum albumin when compared to the first polypeptide and/or can have enhanced pharmacokinetic properties when compared to the first polypeptide. In the case of enhanced pharmacokinetic properties, such properties can be increased serum half-life.

In a second aspect, disclosed herein are cells comprising a modified polynucleotide encoding a modified polypeptide, a suppressor tRNA, and a cognate tRNA synthetase, wherein the modified polynucleotide comprises one or more nonsense codons recognized by the suppressor tRNA, and the cognate tRNA synthetase, wherein the modified polypeptide comprises one or more non-natural amino acids at positions encoded by the nonsense codons, and wherein the non-natural amino acids comprise a moiety selected from the group consisting of: an albumin-targeting group, a radiolabel, and a radiolabelled albumin-targeting group. The nonsense codon can be an amber, opal, or ochre nonsense codon. The non-natural amino acid can comprise an albumin targeting group, and can be, for example, Nε-(4-(4-iodophenyl)butanoyl)lysine, Nε-(4-(4-iodophenyl)butanethioyl)lysine, or pharmaceutically acceptable salts thereof. The non-natural amino acid can comprise a radiolabel, such as $^{123}$I, $^{124}$I, $^{125}$I or $^{131}$I. In one embodiment, the non-natural amino acid is selected from the group consisting of:

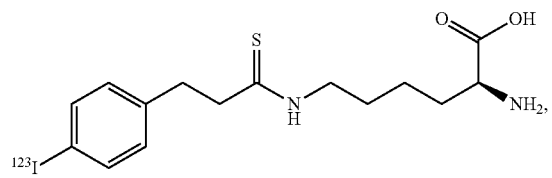
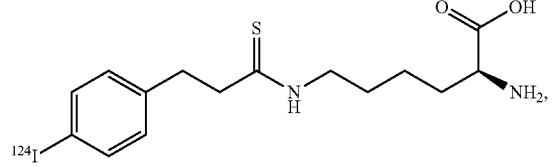
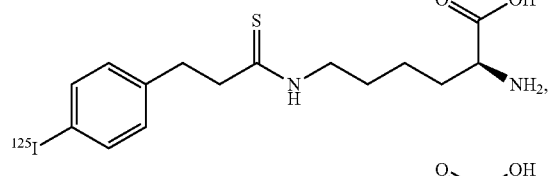
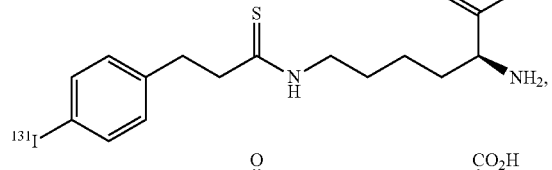
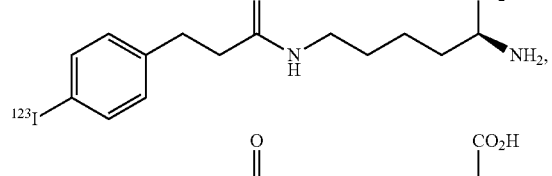
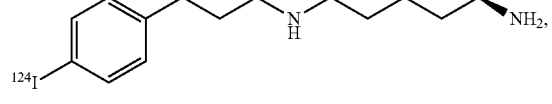

and pharmaceutically acceptable salts thereof.

The non-natural amino acid can comprise a radiolabel, such as $^{123}$I, $^{124}$I, $^{125}$I or $^{131}$I. The non-natural amino acid can also be selected from the group consisting of:

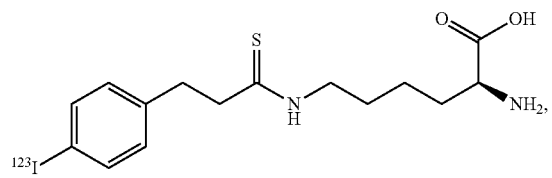
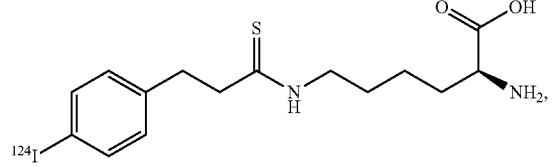
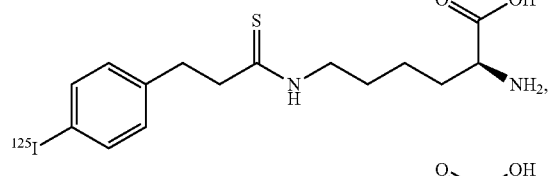
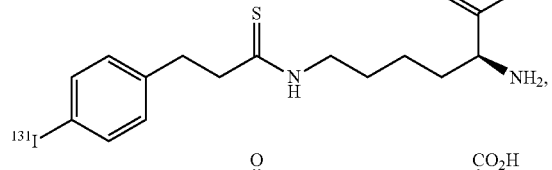
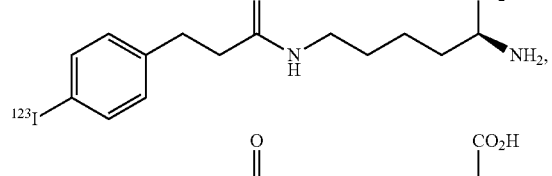
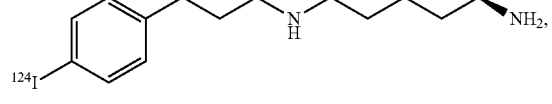

and pharmaceutically acceptable salts thereof.

In this second aspect, the tRNA can be tRNA$_{CUA}^{Pyl}$ and its cognate tRNA synthetase is pyrrolysyl-tRNA synthetase. The cell can be radiation resistant, and can be a bacterial cell, a fungal cell, a plant cell, or a mammalian cell, such as a bacterial *Escherichia coli* cell or a fungal *Saccharomyces cerevisiae* cell. In the case of a bacterial cell, the RecA, YfjK, and DnaB proteins in the cell can be mutated. The *E. coli* cell can be derived from *E. coli* strain C321.ΔA. In the case of an *E. coli* bacterial cell, the mutations can be RecA (D276N); YfjK (A151D); and DnaB (P80H). In the case of a bacterial cell, the cell can comprise only nonsense codons that are not the nonsense codon present in the polynucleotide and/or not express factors that decode the nonsense codon present in the polynucleotide; for example, the cell can comprise a nonsense codon that is an amber nonsense codon, and the factor is release factor-1. In such second aspect, the first polypeptide can be a therapeutic polypeptide, such as one selected from the group consisting of anticoagulants, blood factors, bone morphogenetic proteins, engineered protein scaffolds, enzymes, growth factors, hormones, interferons, interleukins, and thrombolytics. The therapeutic polypeptide can be an antigen-binding polypeptide, such as one selected from the group consisting of an antibody, a chimeric antibody, a monoclonal antibody, a single chain antibody, Fab, Fab', F(a')$_2$, Fv, and scF. In other sub-aspects, the therapeutic polypeptide is an Fc fusion. The therapeutic polypeptide can be an interleukin-1 receptor antagonist. In this second aspect, the non-natural amino acid can comprise an albumin-targeting group. The modified polypeptide of this second aspect can have enhanced binding to human serum albumin when compared to the first polypeptide; furthermore, the modified polypeptide can have enhanced pharmacokinetic properties when compared to the first polypeptide, such as increased serum half-life.

In a third aspect, disclosed herein are methods of making a modified polypeptide that binds to albumin, comprising:

(a) selecting at least one amino acid residue in a first polypeptide to be substituted with a non-natural amino acid disclosed herein;

(b) selecting a polynucleotide encoding the polypeptide;

(c) modifying the polynucleotide such that the amino acid residue to be substituted is encoded by a nonsense codon;

(d) expressing the modified polynucleotide in a cell, wherein the cell is in the presence of the non-natural amino acid, and expresses a suppressor tRNA and its cognate tRNA synthetase, wherein the suppressor tRNA recognizes the nonsense codon of step (c), and the cell incorporates the non-natural amino acid into a modified polypeptide at the nonsense codon of step (c) during translation. The method can further comprise a set (e), purifying the modified polypeptide. The nonsense codon can be an amber, opal, or ochre nonsense codon. The non-natural amino acid can be radiolabelled, such as with $^{123}$I, $^{124}$I, $^{125}$I or $^{131}$I. The suppressor tRNA can be tRNA$_{CUA}^{Pyl}$ and its cognate tRNA synthetase is pyrrolysyl-tRNA synthetase. The cell can be radiation resistant, and can be a bacterial cell, a fungal cell, a plant cell, or a mammalian cell. The cell can be a bacterial *Escherichia coli* cell, or a fungal *Saccharomyces cerevisiae* cell. In the case of a radiation-resistant bacterial cell, the RecA, YfjK, and DnaB proteins in the cell can be mutated, including the mutations RecA (D276N); YfjK (A151D); and DnaB (P80H). The bacterial cell can be derived from *E. coli* strain C321.ΔA. In the case of a bacterial cell, the cell can comprise only nonsense codons that are not the nonsense codon present in the polynucleotide. The bacterial cell can also not express factors that decode the nonsense codon present in the polynucleotide; for example, the nonsense codon present in the nucleotide can be an amber nonsense codon, and the factor can be release factor-1. The first polypeptide can be a therapeutic polypeptide, such as one selected from the group consisting of anticoagulants, blood factors, bone morphogenetic proteins, engineered protein scaffolds, enzymes, growth factors, hormones, interferons, interleukins, and thrombolytics. The therapeutic polypeptide can also be an antigen-binding polypeptide, such as one selected from the group consisting of an antibody, a chimeric antibody, a monoclonal antibody, a single chain antibody, Fab, Fab', F(ab')$_2$, Fv, and scF. The therapeutic polypeptide can be a Fc fusion. The therapeutic polypeptide can be an interleukin-1 receptor antagonist. In such third aspect, the modified polypeptide can have enhanced binding to human serum albumin when compared to the first polypeptide. Furthermore, the modified polypeptide can have enhanced pharmacokinetic properties when compared to the unmodified polypeptide, including increased serum half-life.

In a fourth aspect, disclosed herein are methods of engineering an *Escherichia coli* cell to be resistant to radiation, wherein the cell is used to introduce radiolabeled non-natural amino acids into polypeptides, comprising mutating one or more proteins in the cell. The mutated proteins can comprise RecA, YfjK, and DnaB proteins, and can have mutations RecA (D276N); YfjK (A151D); and DnaB (P80H). The radiolabeled amino acids can be labeled with, for example, $^{123}$I, $^{124}$I, $^{125}$I or $^{131}$I. In such fourth aspect, being resistant to radiation comprises increased survival of the engineered cell compared to a same cell that is not engineered.

In a fifth aspect, disclosed herein are cells, comprising a polynucleotide encoding a first polypeptide that when expressed by the cell is substituted with a non-natural amino acid comprising an albumin targeting group at a nonsense codon in the polynucleotide, creating a modified second polypeptide, wherein:

the cell comprises a suppressor tRNA and its cognate tRNA synthetase that recognize the nonsense codon;

the non-natural amino acid is introduced into the first polypeptide by a nonsense codon;

the non-natural amino acid is exogenously supplied; and the modified second polypeptide has enhanced binding to human serum albumin when compared to the first polypeptide. In one embodiment, the albumin targeting group is selected from the group consisting of:

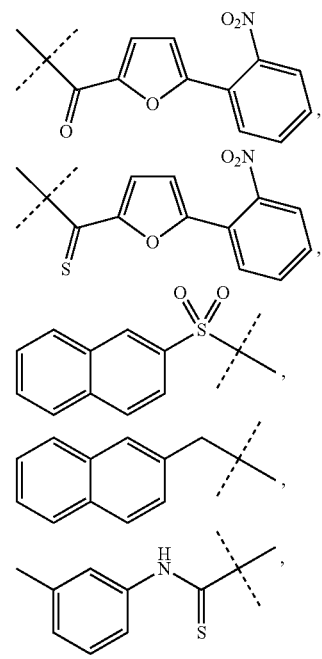

-continued

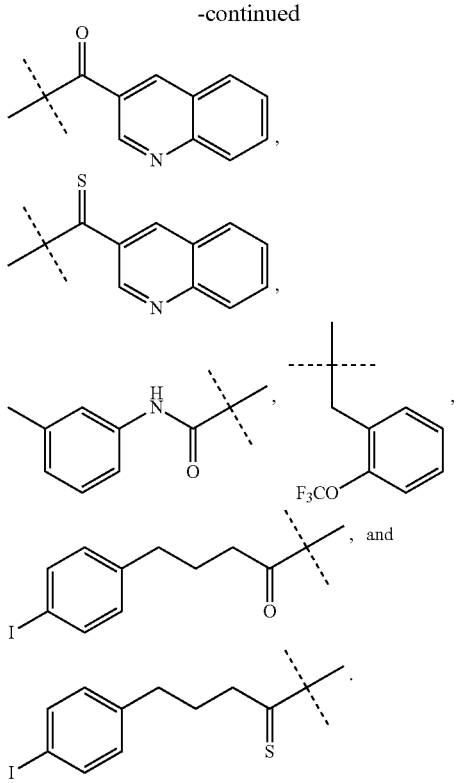

In another embodiment, the albumin targeting group comprises an aryl or heteroaryl moiety and a thioyl moiety, such that the non-natural amino acid comprises a thioamide moiety. In a particular embodiment, the thioyl moiety is conjugated to the aryl or heteroaryl moiety.

The nonsense codon can be an amber, opal, or ochre nonsense codon. The cells can further lack a factor that decodes the nonsense codon recognized by the tRNA. The non-natural amino acid can be Nε-(4-(4-iodophenyl)butanoyl)lysine, and the non-natural amino acid can comprise a radiolabel, such as in the case of Nε-(4-(4-iodophenyl) butanoyl)lysine, the radio label can be $^{123}$I, $^{124}$I, $^{125}$I or $^{131}$I. The cell can be radiation resistant, and can be a bacterial cell, a fungal cell, a plant cell, or a mammalian cell. The cell can be a bacterial Escherichia coli cell, or a fungal Saccharomyces cerevisiae cell. In the case of a radiation-resistant bacterial cell, the RecA, YfjK, and DnaB proteins in the cell can be mutated, including the mutations RecA (D276N); YfjK (A151D); and DnaB (P80H). The bacterial cell can be derived from E. coli strain C321.ΔA. In the case of a bacterial cell, the cell can comprise only nonsense codons that are not the nonsense codon present in the polynucleotide. The bacterial cell can also not express factors that decode the nonsense codon present in the polynucleotide; for example, the nonsense codon present in the nucleotide can be an amber nonsense codon, and the factor can be release factor-1.

In a sixth aspect, disclosed herein is a modified interleukin-1 receptor antagonist polypeptide comprising at least one non-natural amino acid, wherein the non-natural amino acid comprises a moiety selected from the group consisting of: an albumin-targeting group, a radiolabel, and a radiolabelled albumin-targeting group. The modified interleukin-1 receptor antagonist can be human having a polypeptide sequence of SEQ ID NO:1, and the non-natural amino acid is located at position 71, 93, or 135 of the polypeptide of SEQ ID NO:1. The non-natural amino acid can be radiolabelled, such as with $^{123}$I, $^{124}$I, $^{125}$I or $^{131}$I. The modified interleukin-1 receptor antagonist polypeptide can have enhanced binding to human serum albumin when compared to an unmodified interleukin-1 receptor antagonist polypeptide; it may also have pharmacokinetic property can comprise enhanced serum half-life.

In a seventh aspect, disclosed herein are methods of making a modified polypeptide comprising (a) selecting at least one amino acid residue in a first polypeptide to be substituted with a non-natural amino acid, wherein the substituted amino acid is solvent-accessible;

(b) selecting a polynucleotide encoding the first polypeptide;

(c) modifying the polynucleotide such that the amino acid residue to be substituted is encoded by a nonsense codon; and (d) expressing the modified polynucleotide in a cell, wherein the cell is in the presence of the non-natural amino acid and expresses a suppressor tRNA and its cognate tRNA synthetase wherein the suppressor tRNA recognizes the nonsense codon of step (c), and the cell incorporates the non-natural amino acid into a modified polypeptide at the nonsense codon of step (c) during translation. The method can further comprise a set (e), purifying the modified polypeptide. The non-natural amino acid can comprise a moiety selected from the group consisting of: an albumin-targeting group, a radiolabel, and a radiolabelled albumin-targeting group. The suppressor tRNA can be $tRNA_{CUA}^{Pyl}$ and its cognate tRNA synthetase is pyrrolysyl-tRNA synthetase.

In an eighth aspect, disclosed herein are compositions comprising a plurality of identical polypeptides, wherein each polypeptide comprises one or more non-natural amino acids, and wherein the non-natural amino acids comprise a moiety selected from the group consisting of: an albumin-targeting group, a radiolabel, and a radiolabelled albumin-targeting group. In such compositions, the non-natural amino acids can comprise an albumin-targeting group. The one or more non-natural amino acids can be Nε-(4-(4-iodophenyl)butanoyl)lysine. The non-natural amino acids can comprise a radiolabel, such as $^{123}$I, $^{124}$I, $^{125}$I or $^{131}$I.

In a ninth aspect, disclosed herein is a non-natural amino acid compound comprising lysine or ornithine and an albumin targeting group, wherein the lysine or ornithine is linked to the albumin-targeting group by a thioamide moiety (i.e., a thioamide linkage). In certain embodiments, the thioamide linkages are more stable to in vivo hydrolysis, as compared to amide linkages. In certain embodiments, the thioamide linkages are more stable to peptidase activity, as compared to amide linkages. In certain embodiments, the non-natural amino acid compound has greater in vivo stability than a corresponding compound wherein a lysine or ornithine is linked to an albumin-targeting group by an amide moiety.

DETAILED DESCRIPTION

Figure 1:
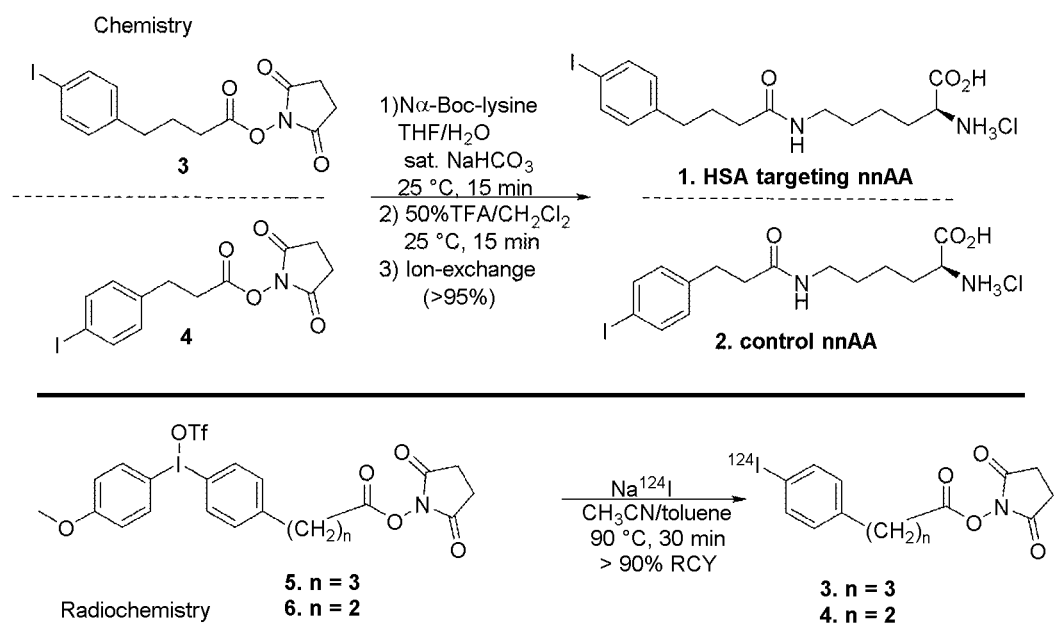
FIG. 1 shows non-natural amino acid syntheses (top) and radiosyntheses (bottom) of compounds disclosed herein.

Disclosed herein are flexible methods to engineer plasma protein binding capability into polypeptides that maintain the advantages of genetic control, but causes a structural perturbation that is commensurate with that of a small molecule tag. By expanding the genetic code to permit introduction of an albumin-targeting amino acid, such as Nε-(4-(4-iodophenyl)butanoyl)lysine, directly into therapeutic proteins meets these requirements. Further disclosed is a simple "toolkit" comprising (1) albumin-targeting, non-natural amino-acids (e.g., lysine or ornithine derivatives); (2) the genetic machinery and modified organisms to introduce this amino acid into therapeutic proteins, and (3) true iodinated radiotracers of therapeutic proteins that permit direct assessment of the impact of the albumin-targeting groups in vivo, where the term "true radiotracer" is defined as a compound which differs from the parent protein only by isotopic substitution of iodine.

Definitions

An "engineered" cell is a cell that differs in at least one property from a parent cell. These differences can come about due to changes in the genetic material and/or content of the cell. In some cases, this change in genetic material is through the introduction of exogenous genetic material, such as is possible through recombinant procedures.

"Enhanced binding" means the binding between at least two molecules, wherein at least one molecule is changed from its native state so that the binding affinity is greater between the two molecules. For example, molecule A may not bind or weakly bind to molecule B, but when molecule A is modified (A'), such as by the introduction of a non-natural amino acid having an affinity tag added thereto, molecule A' binds with greater affinity for molecule B. In the methods and compositions of the invention, molecule A' is a polypeptide modified with a non-natural amino acid with an albumin-binding tag, such as Nε-(4-(4-iodophenyl)butanoyl)lysine, and molecule B is albumin, such as human serum albumin. Enhanced binding can be measured using a variety of techniques, including affinity determination by surface plasmon resonance and direct binding assays "Enhanced pharmacokinetic properties" means that a modified molecule, when compared to the native molecule, differs in at least one pharmacokinetic property. Pharmacokinetic metrics include dose, dosing interval, plasma concentration after administration and the time to reach such; concentration, elimination half-life, elimination rate constant, infusion rate, clearance, bioavailability, fluctuation, etc. For example, an enhanced pharmacokinetic property may include longer serum half-life.

"Expression system" means a host cell, or cellular components and compatible vector under suitable conditions, e.g., for the expression of a protein coded for by foreign DNA carried by the vector and introduced to the host cell. Common expression systems include E. coli host cells and plasmid vectors, insect host cells such as Sf9, Hi5 or S2 cells and Baculovirus vectors, and mammalian host cells and vectors. Other expression systems make use of fungal host cells (such as Saccharomyces cerevisiae) and plant host cells.

Certain embodiments disclosed herein expressly utilize only a cell-free expression or translation system and not a host cell. Certain other embodiments expressly utilize only an auxotrophic host cell. Still certain other embodiments expressly utilize only a non-auxotrophic host cell, or a prototrophic host cell.

The terms "isolated," "purified," or "biologically pure" refer to material that is substantially or essentially free from components that normally accompany it as found in its native state.

The term "subject" refers to a mammal. A subject therefore refers to, for example, dogs, cats, horses, cows, pigs, guinea pigs, and the like. Preferably the subject is a human. When the subject is a human, the subject may be referred to herein as a patient.

Various methodologies of the instant invention include steps that involve comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing a methodology, as described herein. For example, a transcription rate, mRNA level, translation rate, protein level, biological activity, cellular characteristic or property, genotype, phenotype, etc. can be determined prior to performing a methodology. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

A "non-natural amino acid" (nnAA) is an amino acid that is not a member of the canonical 20 amino acids normally encoded by the genetic code. Such nnAAs are organic compounds that have structures similar to a natural amino acid but have been modified structurally to mimic the structure and reactivity of a natural amino acid. nnAAs can share backbone structures, and/or even the most side chain structures of one or more natural amino acids, with the only difference(s) being containing one or more modified groups in the molecule. nnAAs thus include, for example, amino acids or analogs of amino acids other than the 20 naturally-occurring amino acids and include Nε-(3-(4-iodophenyl) propanoyl)lysine and Nε-(4-(4-iodophenyl)butanoyl)lysine.

The term "thioyl" refers to a divalent chemical functional group that is conventionally represented as a carbon atom having a double bond to a sulfur atom.

A "non-sense" codon means a nucleotide triplet that in most organisms does not encode an amino acid. The term is synonymous with "stop codon" and "termination codon." There are three stop codons, amber, ochre and opal. In RNA, they are respectively UAG, UAA, and UGA; in DNA, they are respectively TAG, TAA, and TGA.

Compounds

In an aspect, compounds are disclosed herein that comprise albumin targeting groups. An "albumin targeting group," "albumin targeting molecule," or "albumin targeting tag" is a small molecule that is incorporated into a second molecule, such as a polypeptide, such that the small molecule directs the second molecule to associate with albumin, in vitro or preferably in vivo. Such association comprises a binding interaction between the albumin and the albumin targeting tag. In one embodiment, the albumin targeting group comprises an aryl or heteroaryl moiety and a thioyl moiety, such that the non-natural amino acid (e.g., A-T, as described herein) comprises a thioamide moiety. In a particular embodiment, the thioyl moiety is conjugated to the aryl or heteroaryl moiety.

Exemplary albumin targeting groups are shown in Scheme 1 below (Dumelin C E, et al. *Angew Chem, Int Ed.* 2008; 47, 3196-201; WO2008053360). Other such albumin targeting tags are disclosed in Koehler, M F T, et al. (*Bioorg. Med. Chem. Lett.* 2002, 12:2883); and in Zobel, K., et al. (*Bioorg. Med. Chem. Lett.* 2003. 13:1513). Preferably, the albumin is human serum albumin.

Scheme 1. Small molecule albumin affinity tags.

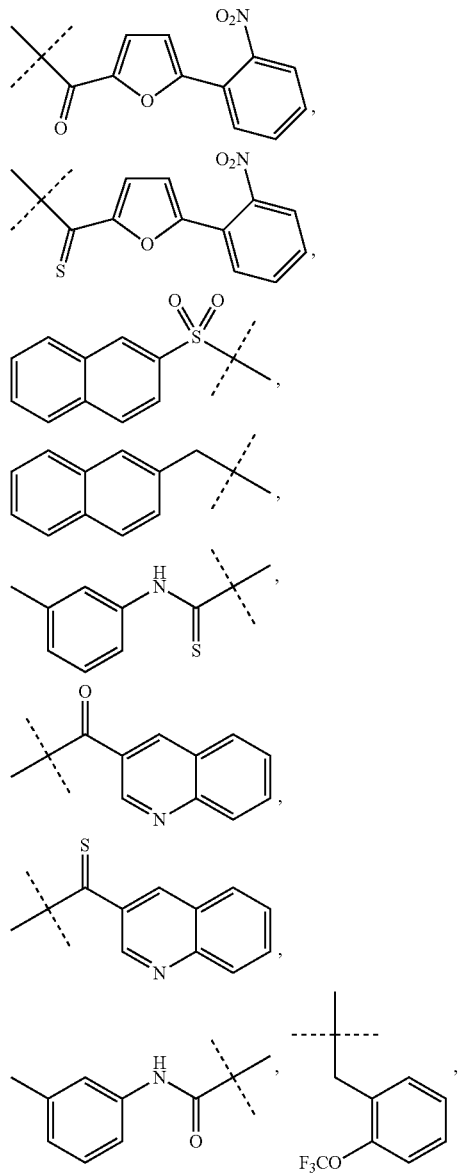

-continued

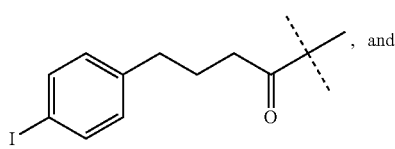, and

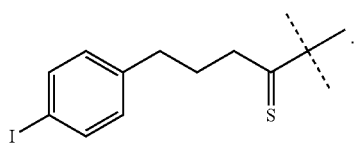.

To assess albumin binding, any assay designed to measure albumin binding can be used. Chromatographic binding assays are especially useful, such as that described by Hage, D S, et al. J (Chromatogr B Biomed Sci Appl. 2000, 739:39-54). Alternatively or in conjunction, binding affinity to albumin can be determined by using surface plasmon resonance. In one method, a BIAcore 200 device (BIAcore Inc.; Piscataway, N.J.) is used in combination with a procedure by Lacy, S E, et al. (MAbs, 2015. 7:605-19) as modified herein. Briefly, human and mouse albumin are captured on a CM5 chip using amine coupling at 5000 resonance units. The candidate polypeptides are injected at various concentrations (e.g., 0, 0.625, 1.25, 5, and 10 μM) at a controlled flow rate (e.g., 20 μl/min). The bound peptides are allowed to dissociate for a period of time (e.g., 5 min) before matrix regeneration using 10 mM glycine, pH 3. The signal from an injection passing over an uncoupled cell is subtracted from that of an immobilized cell to generate sensorgrams of the amount of polypeptide bound as a function of time. BIAcore kinetic evaluation software (version 3.1) can be used to determine $K_D$ from the association and dissociation rates using a one-to-one binding model. Alternatively or in conjunction, affinity to albumin can be determined using a direct assay, such as described by Nguyen, A, et al. (Protein Eng Des Sel. 2006, 19:291-7). In this method, albumin is immobilized onto high protein-binding capacity polystyrene 96 well plates at a predetermined concentration, such as 2 mg/ml, for a period of time (e.g., overnight) at 4° C. Non-specific binding sites are blocked with binding buffer, and radio-labelled candidate polypeptides are applied to the plates for a period of time, such as 30 minutes, at 25° C. Unbound candidate polypeptides are washed away, and bound candidate polypeptides detected using a radioactivity plate reader.

In another aspect, the polypeptides that are targeted to associate with albumin via an albumin targeting molecule comprise at least one amino acid that incorporates the albumin targeting molecule, thus creating a nnAA. Exemplified herein are the nnAAs Nε-(4-(4-iodophenyl)butanoyl)lysine, Nε-(3-(4-iodophenyl)propanoyl)lysine and pharmaceutically acceptable salts thereof (e.g., acid addition salts such as hydrochloride). See, e.g., the compounds of Scheme 2. Nε-(3-(4-iodophenyl)propanoyl)lysine binds albumin poorly, while Nε-(4-(4-iodophenyl)butanoyl)lysine, having a proper albumin binding tag, strongly associates with albumin.

Scheme 2. Non-natural amino acids

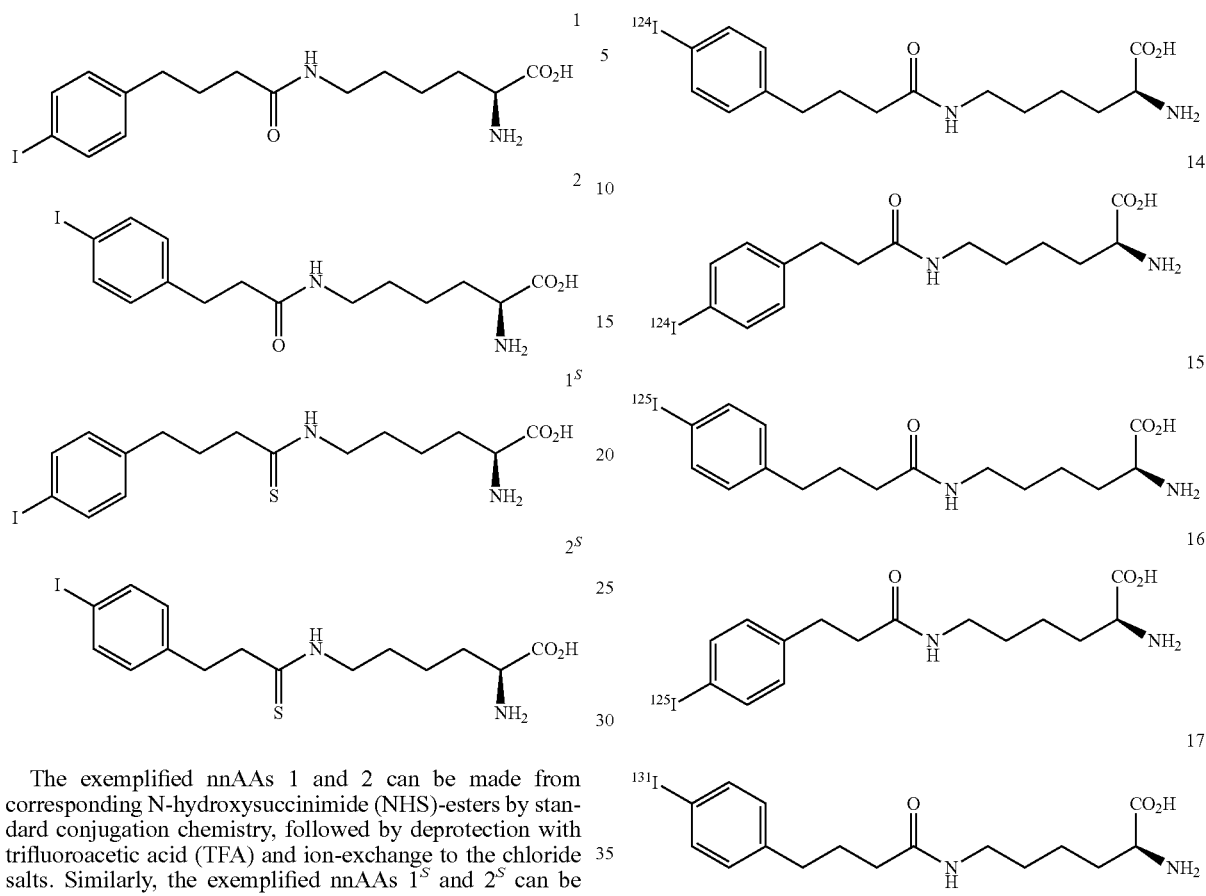

The exemplified nnAAs 1 and 2 can be made from corresponding N-hydroxysuccinimide (NHS)-esters by standard conjugation chemistry, followed by deprotection with trifluoroacetic acid (TFA) and ion-exchange to the chloride salts. Similarly, the exemplified nnAAs $1^S$ and $2^S$ can be made by condensing protected lysine with the corresponding thionacid derivatives of nitrobenzotriazole followed by deprotection and ion-exchange (See, e.g., Thiopeptide Synthesis. Alpha-Amino Thioacid Derivatives of Nitrobenzotriazole as Thioacylating Agents, M. Ashraf Shalaby, Christopher W. Grote, and Henry Rapoport, J. Org. Chem., 1996, 61, 9045-9048).

In some embodiments, the nnAAs are radiolabelled. For example, radioiodinated nnAA analogues comprising $^{123}$I, $^{124}$I, $^{125}$I and $^{131}$I are shown in Scheme 3. The syntheses of radioiodinated non-natural amino acids are performed analogously to the syntheses of non-natural amino acids 1-4 (see, e.g., Example 1).

Scheme 3. Radioiodinated non-natural amino acids

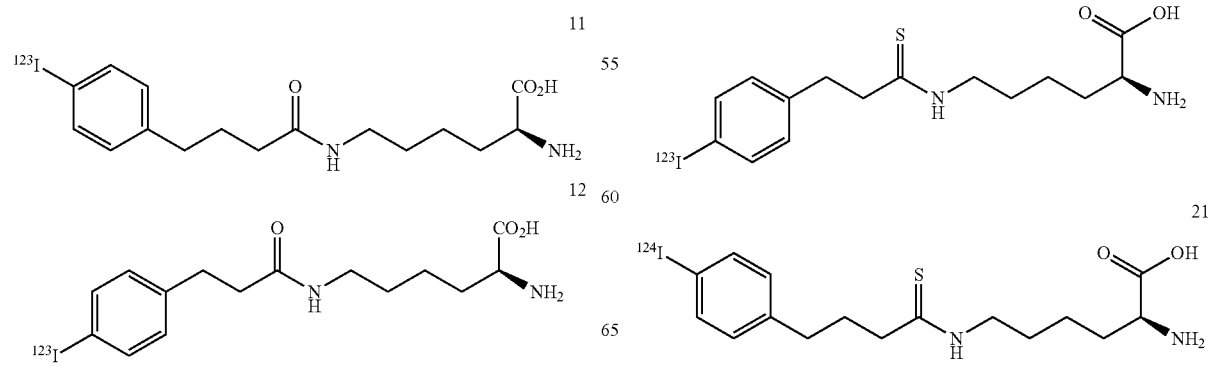

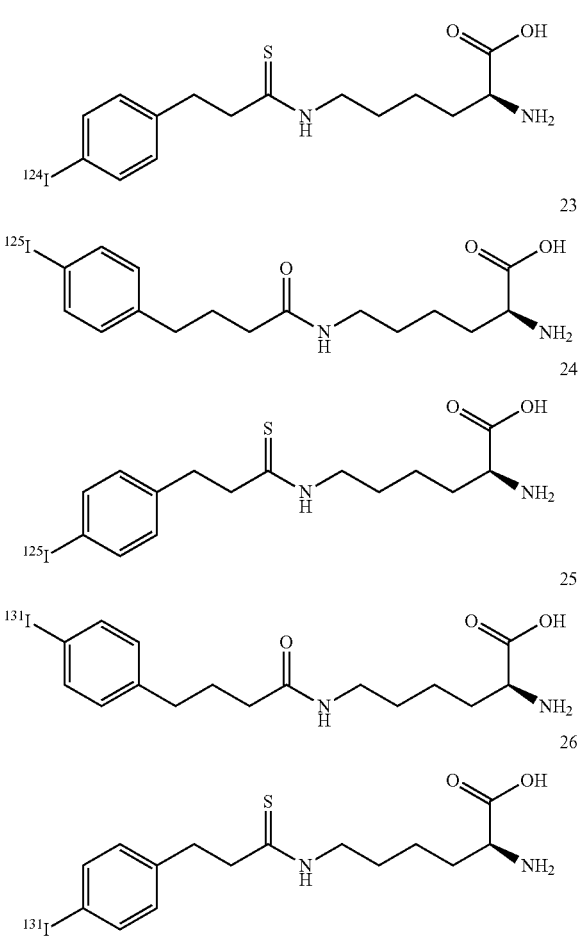

The radiolabel can be selected by one of skill in the art and will depend in part on the type of preferred isotope, the purpose of the radiolabelled polypeptide, the half-life of the isotope, the cost of the isotope, and the facility with which to add the radiolabel to the molecule at a desired location. nnAAs can be purified after radiolabelling using standard techniques.

Particularly with Nε-(4-(4-iodophenyl)butanoyl)lysine, it can be advantageous for the surrounding residues to be modified. The surrounding residues are within two residues to each side of the nnAA. Such a "molecular context" can enhance the binding of the targeted molecule to albumin. Amino acid substitutions can be accomplished by engineering a polynucleotide encoding the polypeptide of interest using techniques common in the art to introduce mutations to randomize these surrounding that encoding the nnAA. Methods include site-directed mutagenesis or PCR-mediated mutagenesis. Upon construction of the desired mutant polynucleotides, the encoded proteins can be expressed and tested for enhanced binding to albumin, using such assays as are described above.

Compositions

In some embodiments, herein disclosed are cells comprising a polynucleotide encoding a first polypeptide that when expressed by the cells are substituted with a radiolabelled non-natural amino acid at a nonsense codon in the polynucleotide, creating a radiolabelled modified polypeptide, wherein: the cells comprise a suppressor tRNA and its cognate tRNA synthetase that recognize the nonsense codon; the non-natural amino acid is introduced into the first polypeptide by a nonsense codon; and the radiolabelled non-natural amino acid is exogenously supplied.

In other aspects, disclosed herein are cells comprising a polynucleotide encoding a first polypeptide that when expressed by the cells are substituted with a non-natural amino acid comprising an albumin targeting group at a nonsense codon in the polynucleotide, creating a modified polypeptide, wherein: the cells comprise a suppressor tRNA and its cognate tRNA synthetase that recognize the nonsense codon; the non-natural amino acid is introduced into the first polypeptide by a nonsense codon; the non-natural amino acid is exogenously supplied; and the modified polypeptide has enhanced binding to human serum albumin when compared to the first polypeptide.

In other aspects, disclosed herein are cells comprising a modified polynucleotide encoding a modified polypeptide, a tRNA synthetase, and a cognate tRNA, wherein the modified polynucleotide comprises one or more nonsense codons recognized by the tRNA synthetase and cognate tRNA, wherein the modified polypeptide comprises one or more non-natural amino acids at positions encoded by the nonsense codons, and wherein the non-natural amino acids comprise a moiety selected from the group consisting of: an albumin-targeting group, a radiolabel, and a radiolabelled albumin-targeting group.

In some aspects, disclosed herein are modified interleukin-1 receptor antagonist polypeptides comprising at least one non-natural amino acid, wherein the non-natural amino acid comprises a moiety selected from the group consisting of: an albumin-targeting group, a radiolabel, and a radiolabelled albumin-targeting group.

Methods

In some aspects, disclosed herein are methods of substituting a natural amino acid in a first polypeptide with a non-natural amino acid to obtain a modified polypeptide, wherein the non-natural amino acid comprises a moiety selected from the group consisting of: an albumin-targeting group, a radiolabel, and a radiolabelled albumin-targeting group, comprising:

(a) selecting at least one amino acid residue in the first polypeptide to be substituted with the non-natural amino acid;

(b) selecting a polynucleotide encoding the first polypeptide;

(c) modifying the polynucleotide such that the amino acid residue to be substituted is encoded by a nonsense codon;

(d) expressing the modified polynucleotide in a cell, wherein the cell is in the presence of the non-natural amino acid and expresses a suppressor tRNA and its cognate tRNA synthetase wherein the suppressor tRNA recognizes the nonsense codon of step (c), and the cell incorporates the non-natural amino acid into the modified polypeptide at the nonsense codon of step (c) during translation. The method can optionally further include a purification step (e), wherein the modified polypeptide is purified.

In other aspects, disclosed herein are methods of making a modified polypeptide that binds to albumin, comprising:

(a) selecting at least one amino acid residue in a first polypeptide to be substituted with Nε-(4-(4-iodophenyl)butanoyl)lysine;

(b) selecting a polynucleotide encoding the polypeptide;

(c) modifying the polynucleotide such that the amino acid residue to be substituted is encoded by a nonsense codon;

(d) expressing the modified polynucleotide in a cell, wherein the cell is in the presence of the Nε-(4-(4-iodophenyl)butanoyl)lysine, or a pharmaceutically acceptable salt thereof and expresses a suppressor tRNA and its cognate tRNA synthetase wherein the suppressor tRNA recognizes the nonsense codon of step (c), and the cell incorporates the Nε-(4-(4-iodophenyl)butanoyl)lysine into a modified polypeptide at the nonsense codon of step (c) during translation.

The method can optionally further include a purification step (e), wherein the modified polypeptide is purified.

In another aspect, disclosed herein are methods of engineering a cell, such as an *Escherichia coli* cell, to be resistant to radiation, wherein the cell is used to introduce radiolabeled non-natural amino acids into polypeptides, comprising mutating one or more proteins in the cell.

In another aspect, disclosed herein are methods of making a modified polypeptide comprising (a) selecting at least one amino acid residue in a first polypeptide to be substituted with a non-natural amino acid, wherein the substituted amino acid is solvent-accessible;

(b) selecting a polynucleotide encoding the first polypeptide;

(c) modifying the polynucleotide such that the amino acid residue to be substituted is encoded by a nonsense codon; and (d) expressing the modified polynucleotide in a cell, wherein the cell is in the presence of the non-natural amino acid and expresses a suppressor tRNA and its cognate tRNA synthetase wherein the suppressor tRNA recognizes the nonsense codon of step (c), and the cell incorporates the non-natural amino acid into a modified polypeptide at the nonsense codon of step (c) during translation.

The method can optionally further include a purification step (e), wherein the modified polypeptide is purified.

Selection of a Polypeptide

The selection of a polypeptide for targeting to albumin can be determined by one of skill in the art. In choosing such polypeptides, the polypeptide often has a therapeutic application, which function would benefit from binding to serum albumin to, for example, increase the serum half-life of the therapeutic polypeptide in those embodiments directed to albumin targeting of polypeptides. General examples of therapeutic polypeptides include, but are not limited to, antibodies, chimeric antibodies, monoclonal antibodies, single chain antibodies, Fab, Fab', F(ab')2, Fv, and scF, Fc fusions, anticoagulants, blood factors, bone morphogenetic proteins, engineered protein scaffolds, enzymes, growth factors, hormones, interferons, interleukins, and thrombolytics. Other examples of therapeutic peptides include: salmon calcitonin; beta-interferon; gamma-interferon; veraglucerase-alpha; taliglucerase-alpha; glucarpidase (e.g., for treatment of methotrexate toxicity); elosulfase-alpha (e.g., for treatment of Morquio syndrome); aldesleukin; anakinra; insulin lispro; uricase (e.g., for treatment of gouty tophi); palifermin.

In some aspects, the polypeptide is interleukin-1 receptor antagonist (IL-1RA; SEQ ID NO:1, see Table 1; the mature form lacks the initiation methionine: SEQ ID NO:2). Once modified with a nnAA having an albumin targeting group, such as the nnAA Nε-(4-(4-iodophenyl)butanoyl)lysine, then the modified IL-1RA will have enhanced binding to albumin than the unmodified IL-1RA. In additional aspects, the modified IL-1RA will have enhanced pharmacokinetic properties, such as an increase in serum half-life when administered to a subject.

TABLE 1

Amino acid sequence of IL-1RA

```
Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35              40                  45

Val Val Pro Ile Glu Pro His Ala Leu Phe Leu Gly Ile His Gly Gly
        50              55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150
```

Selection of Non-Natural Amino Acid (nnAA)

In some embodiments of the compositions and methods described herein, the non-natural amino acid comprises a moiety selected from the group consisting of: an albumin-targeting group, a radiolabel, and a radiolabelled albumin-targeting group.

In a particular embodiment, the non-natural amino acid comprises an albumin-targeting group. As described above, a non-natural amino acid comprising an albumin-targeting group exhibits enhanced albumin binding and pharmacokinetic properties relative to the corresponding natural amino acid. Similarly, a polypeptide comprising a non-natural amino acid comprising an albumin-targeting group exhibits enhanced albumin binding and pharmacokinetic properties relative to an analogous polypeptide having a natural amino acid at the same position. For example, a modified polypeptide comprising the non-natural amino acid compound 1 at a particular position in the sequence will exhibit enhanced albumin binding and pharmacokinetic properties relative to the corresponding unmodified polypeptide comprising a lysine at the particular position.

In another particular embodiment, the non-natural amino acid comprises a radiolabeled albumin-targeting group. In a preferred embodiment, the radiolabel is radioiodine (e.g., $^{123}$I, $^{124}$I, $^{125}$I or $^{131}$I). The incorporation of a radiolabel (e.g., a radioiodine) is useful for purposes including investigations of polypeptide metabolism and tissue distribution.

In some embodiments, the nnAA to be chosen for substitution can be represented by the formula A-T, wherein A is an amino acid, and T is a moiety selected from the group consisting of: an albumin-targeting group, a radiolabel, and a radiolabelled albumin-targeting group. In some embodiments, A is selected from the group consisting of lysine, ornithine, arginine, serine, threonine, asparagine and glutamine. In one embodiment, T can be an albumin targeting group selected from Scheme 1 or an albumin targeting group known to one of skill in the art, such as those disclosed by Koehler, M F T, et al. (*Bioorg. Med. Chem. Lett.* 2002, 12:2883) and in Zobel, K., et al. (*Bioorg. Med. Chem. Lett.* 2003. 13:1513).

In a particular embodiment, A is lysine, and T is 4-(4-iodophenyl)butyrate (i.e., A-T is compound 1, as shown in Scheme 2). In another particular embodiment, the nnAA is selected from the species of Scheme 2 or Scheme 3.

Selection of Amino Acid Residue(s) to be Substituted with a nnAA

The selection of the amino acid residue(s) to be substituted is determined in part depending on the secondary and tertiary structure of the target polypeptide and the function of the target polypeptide. The objective, as understood by one of skill in the art, is to substitute with a nnAA at permissive sites in the polypeptide, such that the secondary and tertiary structure of the polypeptide is minimally disturbed, if at all, and the function of the polypeptide is not significantly decreased. Preferred locations include those residues that are on the surface of the target polypeptide, those that are solvent accessible, those that are away from any active or co-factor site (such as in the case of enzymes) or binding site (such as in the case of receptor/ligand polypeptides).

Furthermore, the use of conservative amino acid substitutions can be useful to minimally disturb the structure and function of the substituted polypeptide. A "conservative amino acid substitution" is one in which an amino acid residue is substituted by another amino acid residue (including nnAA residues) having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art (Pearson, 1994, *Methods Mol. Biol.* 243:307-31).

Examples of groups of amino acids that have side chains with similar chemical properties include (1) aliphatic side chains: glycine, alanine, valine, leucine, and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartic acid and glutamic acid; and (7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., 1992, *Science* 256:1443-1445. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, Genetics Computer Group (GCG available from Genetics Computer Group, Inc.), also referred to as the Wisconsin Package, is an integrated software package of over 130 programs for accessing, analyzing and manipulating nucleotide and protein sequences. GCG contains programs such as "Gap" and "Bestfit" which can be used with default parameters to determine sequence similarity, homology and/or sequence identity between closely related polypeptides, such as homologous polypeptides from different species of organisms or between a wild type protein and a mutein thereof. See, e.g., GCG version 6.1, version 7.0, version 9.1, and version 10.0.

Polypeptide sequences also can be compared using FASTA, a program in GCG, using default or recommended parameters. FASTA (e.g., FASTA2 and FASTA3) provides alignments and percent sequence identity of the regions of the best overlap between the query and search sequences (Pearson, 1990, *Methods Enzymol.* 183:63-98; Pearson, 2000, *Methods Mol. Biol.* 132:185-219). Another preferred algorithm when comparing a sequence of the invention to a database containing a large number of sequences from different organisms is the computer program BLAST, especially blastp or tblastn, using default parameters. See, e.g., Altschul et al., 1990, *J. Mol. Biol.* 215:403-410; Altschul et al., 1997, *Nucleic Acids Res.* 25:3389-402.

As an example, in the case of human interleukin 1 receptor antagonist (IL-1RA; SEQ ID NO:1), where the nnAA Nε-(4-(4-iodophenyl)butanoyl)lysine is desired to be incorporated, permissive sites include Asn 135 (a conservative substitution), Lys71 and Lys93 (both chosen in part because the selected nnAA is a derivative a lysine) because these sites are on the surface of the polypeptide, are solvent accessible, and do not interfere with IL-1RA binding to interleukin 1 receptor (IL-1R).

Selection of Polynucleotide

The polynucleotides selected for use with the methods disclosed herein are those that encode the target polypeptides to be modified by incorporation of a nnAA. Such polynucleotides can be obtained in a variety of ways, including traditional cloning techniques and polynucleotide synthesis. These approaches and others are well within the skill of a person in the art.

Polynucleotide Modification and Expression Systems

To incorporate the nnAA, one approach is to create a system wherein a usual non-sense codon, such as an amber codon, is used to encode for the nnAA. Other codons that can be used include the opal and ochre nonsense codons.

An expression system useful in the methods disclosed herein will comprise: (1) a nnAA, (2) an expression system, (3) a tRNA synthetase, (4) the cognate tRNA of the tRNA synthetase, and (5) a polynucleotide to be expressed that comprises the nonsense codon recognized by the tRNA. For example, U.S. Pat. No. 8,980,581 discloses the building and use of expression systems incorporating nnAAs.

The polynucleotide to be expressed can be modified by a number of techniques to engineer the desired nonsense codon at the desired location. For example, site-directed mutagenesis and PCR-mediated mutagenesis can be used.

Host cells are genetically engineered with polynucleotide vectors, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods. Transformation methods are well known in the art. For example, several well-known methods of introducing target nucleic acids into bacterial cells are available. These include: fusion of the recipient cells with bacterial protoplasts containing the DNA, electroporation, projectile bombardment, and infection with viral vectors.

Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

The expression system can be chosen such that the nonsense codon the suppressor tRNA recognizes in the host cell is replaced in the native genome with other nonsense codons. In other aspects, the expression system can be chosen such that the host cell lacks a release factor that decodes the nonsense codon as the termination signal of protein translation. In yet another aspect, the host cell both lacks a nonsense codon, such as an amber codon, and lacks release factor1, which decodes the amber codon as the termination signal.

Host cells can also be radiation resistant. In such aspects, the host cell can be a bacterial cell; which, in some embodiments, is an $E.$ $coli$ cell. In the case of an $E.$ $coli$ cell, the cell is engineered to comprise mutations in RecA (D276N), YfjK (A151D), and DnaB (P80H). In some aspects, the $E.$ $coli$ cell to be engineered is C321.ΔA (available as strain 48998 from Addgene; Cambridge, Mass.).

Aminoacyl tRNA synthetases (AARSs) catalyze the aminoacylation reaction for incorporation of amino acids into proteins via the corresponding transfer RNA molecules. Precise manipulation of synthetase activity can alter the aminoacylation specificity to stably attach non-canonical amino acids into the intended tRNA. Then, through codon-anticodon interaction between message RNA (mRNA) and tRNA, the amino acid analogs can be delivered into a growing polypeptide chain. Thus, incorporation of non-natural amino acids into proteins relies on the manipulation of amino acid specificity of AARS.

The AARS (or "synthetase") can be a naturally occurring synthetase derived from an organism, whether the same (homologous) or different (heterologous), a mutated or modified synthetase, or a designed synthetase.

The synthetase can recognize the desired nnAA selectively over available related amino acids. For example, when the amino acid analog to be used is structurally related to a naturally occurring amino acid (e.g., lysine and Nε-(4-(4-iodophenyl)butanoyl)lysine), the synthetase should charge the external mutant tRNA molecule with the desired nnAA with an efficiency at least substantially equivalent to that of, and more preferably at least about twice, 3 times, 4 times, 5 times or more than that of the naturally occurring amino acid.

A synthetase can be obtained by a variety of techniques known to one of skill in the art, including combinations of such techniques as, for example, computational methods, selection (directed evolution) methods, and incorporation of synthetases from other organisms.

In certain embodiments, synthetases can be used or developed that efficiently charge tRNA molecules that are not charged by synthetases of the host cell. For example, suitable pairs may be generally developed through modification of synthetases from organisms distinct from the host cell. The synthetase can also be developed by selection procedures or can be designed using computational techniques such as those described in Datta et al., $J.$ $Am.$ $Chem.$ $Soc.$ 124: 5652-5653, 2002, and in U.S. Pat. No. 7,139,665.

A strategy for generating an external mutant tRNA, modified or external mutant AARS, or modified tRNA/AARS pair involves importing a tRNA and/or synthetase from another organism into the translation system of interest, such as $E.$ $coli.$ The properties of the heterologous synthetase candidate include, e.g., that it does not charge $E.$ $coli$ tRNA reasonably well (preferably not at all), and the properties of the heterologous tRNA candidate include, e.g., that it is not acylated by $E.$ $coli$ synthetase to a reasonable extent (preferably not at all).

A similar approach involves the use of a heterologous synthetase as the external mutant synthetase and a mutant initiator tRNA of the same organism or a related organism as the modified tRNA.

The pairs and components of pairs desired above can be evolved to generate external mutant tRNA and/or AARS that possess desired characteristics, e.g., that can preferentially aminoacylate an O-tRNA with a nnAA.

The modified tRNA and the modified AARS can be derived by mutation of a naturally occurring tRNA and AARS from a variety of organisms. The modified tRNA and/or modified AARS are derived from at least one organism, where the organism is a prokaryotic organism, e.g., $Methanococcus$ $jannaschii,$ $Methanobacterium$ $thermoautotrophicum,$ $Halobacterium,$ $E.$ $coli,$ $A.$ $fulgidus,$ $P.$ $furiosus,$ $P.$ $horikoshii,$ $A.$ $pernix,$ and $T.$ $thermophilus.$ Optionally, the organism is a eukaryotic organism, e.g., plants, algae, fungi, animals, insects, and protists. Optionally, the modified tRNA is derived by mutation of a naturally occurring tRNA from a first organism and the modified AARS is derived by mutation of a naturally occurring AARS from a second organism. The modified tRNA and modified AARS can be derived from a mutated tRNA and mutated AARS. The modified AARS and/or modified tRNA from a first organism can be provided to a translational system of a second organism, which optionally has non-functional endogenous AARS and/or tRNA with respect to the codons recognized by the modified tRNA or modified AARS.

The mutation or modification of an AARS to be used for incorporation of a nnAA into a target polypeptide or protein can be performed by using directed mutagenesis once the desired contact amino acid residues have been identified. Identification of the contact amino acids can be performed using any method that allows analysis of the structure of the AARS, including crystallographic analysis, computer modeling, nuclear magnetic resonance (NMR) spectroscopy, library screening, or a combination of any of these or other methods.

A number of AARS molecules have been sequenced, which sequence information provides guidance as to which amino acids are important for binding the amino acid with which to charge the corresponding tRNA.

In certain embodiments, the AARS capable of charging a particular external mutant tRNA with a particular nnAA can be obtained by mutagenesis of the AARS to generate a library of candidates, followed by screening and/or selection of the candidate AARS's capable of their desired function. Such external mutant AARSs and external mutant tRNAs may be used for in vitro/in vivo production of desired proteins with modified unnatural amino acids.

Methods for producing at least one recombinant external mutant AARS comprise: (a) generating a library of (optionally mutant) AARSs derived from at least one AARS from a first organism, e.g., a eukaryotic organism (such as a yeast), or a prokaryotic organism, such as *Methanococcus jannaschii, Methanobacterium thermoautotrophicum, Halobacterium, E. coli, A. fulgidus, P. furiosus, P. horikoshii, A. pernix*, and *T. thermophilus*; (b) selecting (and/or screening) the library of AARSs (optionally mutant AARSs) for members that aminoacylate an external mutant tRNA in the presence of an unnatural amino acid and a natural amino acid, thereby providing a pool of active (optionally mutant) AARSs; and/or, (c) selecting (optionally through negative selection) the pool for active AARSs (e.g., mutant AARSs) that preferentially aminoacylate the O-tRNA in the absence of the nnAA, thereby providing the at least one recombinant external mutant synthetase, wherein the at least one recombinant external mutant synthetase preferentially aminoacylates the external mutant tRNA with the nnAA.

Libraries of mutant AARSs can be generated using various mutagenesis techniques known in the art. For example, the mutant AARSs can be generated by site-specific mutations, random mutations, diversity generating recombination mutations, chimeric constructs, and by other methods described herein or known in the art.

Selecting (and/or screening) the library of AARSs for members that are active, e.g., that aminoacylate an external mutant tRNA in the presence of a nnAA and a natural amino acid, includes: introducing a positive selection or screening marker, e.g., an antibiotic resistance gene, or the like, and the library of AARSs into a plurality of cells, wherein the positive selection and/or screening marker comprises at least one codon, which translation (optionally conditionally) depends on the ability of a candidate AARSs to charge the external mutant tRNA (with either a natural and/or a unnatural amino acid); growing the plurality of cells in the presence of a selection agent; identifying cells that survive (or show a specific response) in the presence of the selection and/or screening agent by successfully translate the codon in the positive selection or screening marker, thereby providing a subset of positively selected cells that contains the pool of active AARSs.

A cell-free in vitro system can be used to test the ability of the external mutant synthetase to charge the modified tRNA in a positive screening. For example, the ability of the in vitro system to translate a positive screening gene, such as a fluorescent marker gene, may depend on the ability of the external mutant synthetase to charge modified tRNA to read through a codon of the marker gene.

Negatively selecting or screening the pool for active AARSs (optionally mutants) that preferentially aminoacylate the mutant tRNA in the absence of the unnatural amino acid includes: introducing a negative selection or screening marker with the pool of active AARSs from the positive selection or screening into a plurality of translational system, wherein the negative selection or screening marker comprises at least one codon (e.g., codon for a toxic marker gene, e.g., a ribonuclease barnase gene), which translation depends on the ability of a candidate AARS to charge the external mutant tRNA (with a natural amino acid); and, identifying the translation system that shows a specific screening response in a first media supplemented with the unnatural amino acid and a screening or selection agent, but fail to show the specific response in a second media supplemented with the natural amino acid and the selection or screening agent, thereby providing surviving cells or screened cells with the at least one recombinant AARS.

Methods for producing a recombinant external mutant tRNA include: (a) generating a library of mutant tRNAs derived from at least one tRNA, from a first organism; (b) selecting (e.g., negatively selecting) or screening the library for (optionally mutant) tRNAs that are aminoacylated by an AARS (RS) from a second organism in the absence of a AARS from the first organism, thereby providing a pool of tRNAs (optionally mutant); and, (c) selecting or screening the pool of tRNAs (optionally mutant) for members that are aminoacylated by an introduced external mutant AARS, thereby providing at least one recombinant tRNA; wherein the at least one recombinant tRNA recognizes a non-natural amino acid codon and is not efficiency recognized by the AARS from the second organism and is preferentially aminoacylated by the external mutant AARS.

AARS mutants can be generated from a library of mutants already having the desired activity. Mutant AARSs are selected, mutagenized (such as by error-prone PCR) and subjected to positive and negative selection as generally described above. The objective of the positive selection is to identify those mutants that can charge the tRNA with the nnAA; the objective of the negative selection is to rid the identified AARSs from the positive selection that can charge the tRNA with endogenous amino acids. For example, a positive screen is based on a bacterial cell's (such as *E. coli*) resistance to chloramphenicol, which is conferred by the suppression of an amber mutation in the chloramphenicol acetyltransferase gene in the presence of the nnAA. An example of a negative screen is the use of a barnase gene having an amber mutation and is carried out in the absence of the nnAA. tRNA's that can be charged with endogenous amino acids allows for expression of the toxic barnase gene and cells carrying such mutants die.

Suppressor tRNAs can also be optimized, desirable especially when the tRNA is derived from another organism than that derived for the expression system. For example, the nucleotides in the T-stem and A-stem can be randomized, as well as those nucleotides that form Watson-Crick base pairing. tRNA mutants that are positively selected with chloramphenicol are then subjected to a screen to monitor efficiency of the tRNA to incorporate the nnAA, such as where green fluorescent protein (GFP) is engineered with an amber nonsense codon; in the presence of the nnAA and the mutant tRNA, the GFP is expressed, and signal intensity can be used as a guide to understand the ability of the tRNA to incorporate the nnAA into the encoded protein.

In an embodiment, the AARS/tRNA pair is pyrrolysyl-tRNA synthetase (PylRS) and its cognate tRNA$_{CUA}^{Pyl}$ and wherein the nnAA is Nε-(4-(4-iodophenyl)butanoyl)lysine. In an embodiment, PylRS is from methanogenic archaea. PylRS and tRNA$_{CUA}^{Pyl}$ naturally incorporate pyrrolysine in response to the amber nonsense codon in some methanogenic archaea (Blight, S K, et al. *Nature*, 2004: 333-5; Srinivasan, G, et al. *Science*, 2002, 296:1459-62). *E. coli* and animal cell endogenous AARSs do not recognize tRNA$_{CUA}^{Pyl}$ (Polycarpo, C, et al. *PNAS* 2004, 101: 12450-4; Nozawa, K, et al. *Nature*, 2009, 457: 1163-7; Chen, P R, et al. *Angew Chem Int Ed.* 2009, 48:4052-5). Thus nnAA can be added to the genetic code of mammalian cells and bacteria using the tRNA$_{CUA}^{Pyl}$/PylRS pair (Dumas, A., et al. *Chemical Science.* 2015, 6:50-69). In some embodiments, the PylRS is optimized for Nε-(4-(4-iodophenyl)butanoyl) lysine. In other embodiments, the tRNA$_{CUA}^{Pyl}$ is optimized for NE-(4-(4-iodophenyl)butanoyl)lysine. In yet another embodiment, the tRNA$_{CUA}^{Pyl}$/PylRS pair is optimized for Nε-(4-(4-iodophenyl)butanoyl)lysine.

Purification

The modified polypeptides can be purified from the cells and/or the cell media (if the modified polypeptide is secreted by the cells during expression) using well-known techniques. For example, the modified polypeptide can be further modified to comprise an affinity tag, permitting easy purification of the modified polypeptide from the expression system. Tags are typically placed at the polypeptide's N- or C-terminus, where they can be easily removed in subsequent processing.

A frequently used affinity tag is a multi-histidine tag (e.g., 6×His), which has an affinity towards nickel or cobalt ions. If nickel or cobalt ions are immobilized on a solid carrier, such as a resin column, the His-tagged polypeptides can be depleted from a cell lysate or cell media by running the lysate or media through the column. Such techniques are well known in the art, and His-tag vectors are commercially available.

Other affinity tags can be used, which allow rapid removal of the modified polypeptide by immunoaffinity-based separation technique, such as immunoaffinity chromatography. Exemplary tags include Green Fluorescent Protein (GFP), Glutathione-S-transferase (GST), and the FLAG-tag.

Simple immunoaffinity purification, without any tags, can also be used.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1: Amino Acid Synthesis and Radiosynthesis

The two non-natural amino acids (nnAAs 1 and 2; FIG. 1) were synthesized from the corresponding NHS-esters by standard conjugation chemistry (FIG. 1). We performed a chromatographic assay of HSA binding (Hage D S, Austin J. High-performance affinity chromatography and immobilized serum albumin as probes for drug- and hormone-protein binding. *J Chromatogr B Biomed Sci Appl.* 2000; 739, 39-54) for these two tags ($K_d$=7.0 µM for 1; $K_d$=204 µM for 2) and confirmed the significant difference in HSA affinity observed previously (Dumelin C E, et al. A portable albumin binder from a DNA-encoded chemical library. *Angew Chem, Int Ed.* 2008; 47, 3196-201). To establish that radiolabeled 1 and 2 could be prepared on a timescale commensurate with protein biosynthesis, diaryliodonium salt precursors 5 and 6 (FIG. 1) were treated with no-carrier-added (n.c.a.) Na$^{124}$I (2 mCi) to afford $^{124}$I-labeled 3 and 4 in excellent radiochemical yield with little to no hydrolysis of the activated ester. Rapid purification (ethyl acetate, silica sep-pak) provided sufficiently pure material for peptide labeling studies. These results demonstrate that high specific activity $^{125}$I-labeled 1 and 2 can be prepared quickly (within 3 hours) and in sufficient radiochemical yield for same-day biosynthesis of proteins, such as the IL-1RA mutant proteins.

Compounds 5 and 6 were prepared according to, or in analogy to, the method of Example 11.

Example 2: Protein Synthesis Using 1 and 2

Pyrrolysyl-tRNA synthetase (PylRS) and its cognate tRNA$_{CUA}^{Pyl}$ naturally incorporate pyrrolysine (Pyl) in response to the amber nonsense codon in some methanogenic archaea (Blight S K, et al. Direct charging of tRNACUA with pyrrolysine in vitro and in vivo. *Nature.* 2004; 431, 333-5; Srinivasan G, et al. Pyrrolysine Encoded by UAG in Archaea: Charging of a UAG-Decoding Specialized tRNA. *Science.* 2002; 296, 1459-62). Previous work has shown that tRNA$_{CUA}^{Pyl}$ is not recognized by endogenous aminoacyl-t-RNA synthetases (AARSs) in *E. coli* or mammalian cells (Polycarpo C, et al. An aminoacyl-tRNA synthetase that specifically activates pyrrolysine. *Proc Natl Acad Sci USA.* 2004; 101, 12450-4; Nozawa K, et al. Pyrrolysyl-tRNA synthetase-tRNAPyl structure reveals the molecular basis of orthogonality. *Nature.* 2009; 457, 1163-7; Chen P R, et al. A Facile System for Encoding Unnatural Amino Acids in Mammalian Cells. *Angew Chem Int Ed.* 2009; 48, 4052-5), and that non-natural amino acids (nnAAs) can be added to the genetic code of mammalian cells and bacteria using the tRNA$_{CUA}^{Pyl}$/PylRS pair (Dumas A, et al. Designing logical codon reassignment—Expanding the chemistry in biology. *Chemical Science.* 2015; 6, 50-69). More importantly, many of these nnAAs are structurally similar to 1 and 2.

Figure 2:
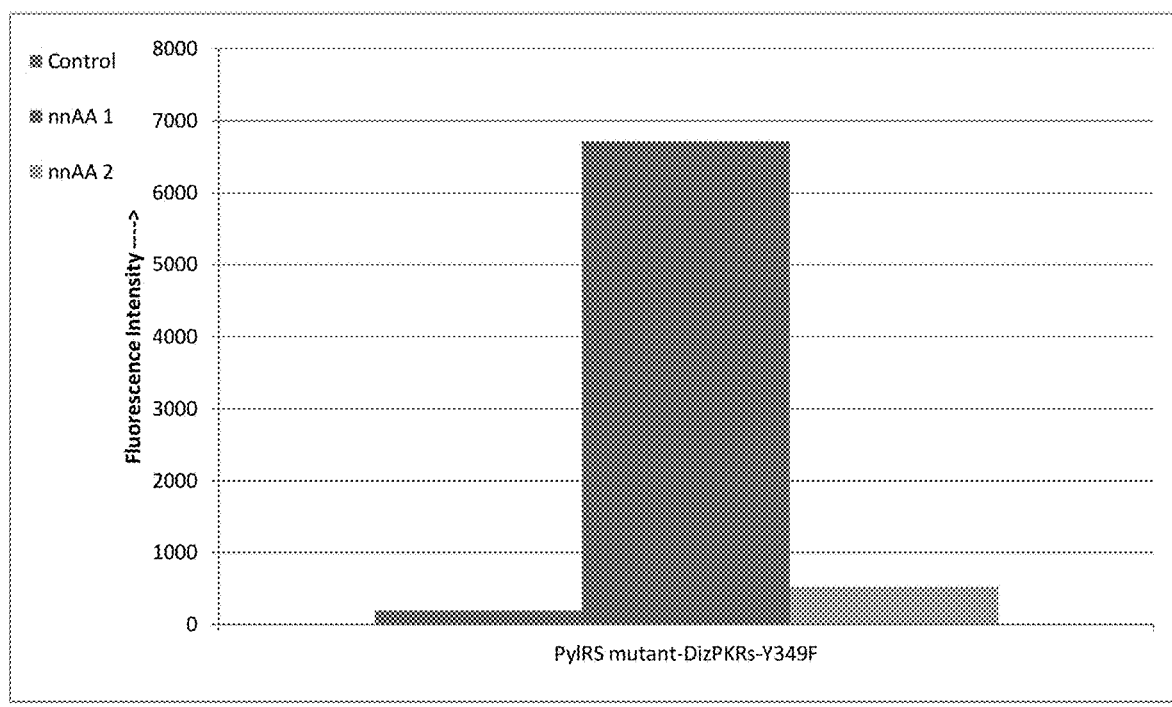
FIG. 2 shows amber suppression in green fluorescent protein (GFP) by a PylRS mutant in the presence of the non-natural amino acid Nε-(4-(4-iodophenyl)butanoyl)lysine. Shown from left to right is a fluorescence intensity histogram for control, mutant nnAA 1, and mutant nnAA2.
Figure 3:
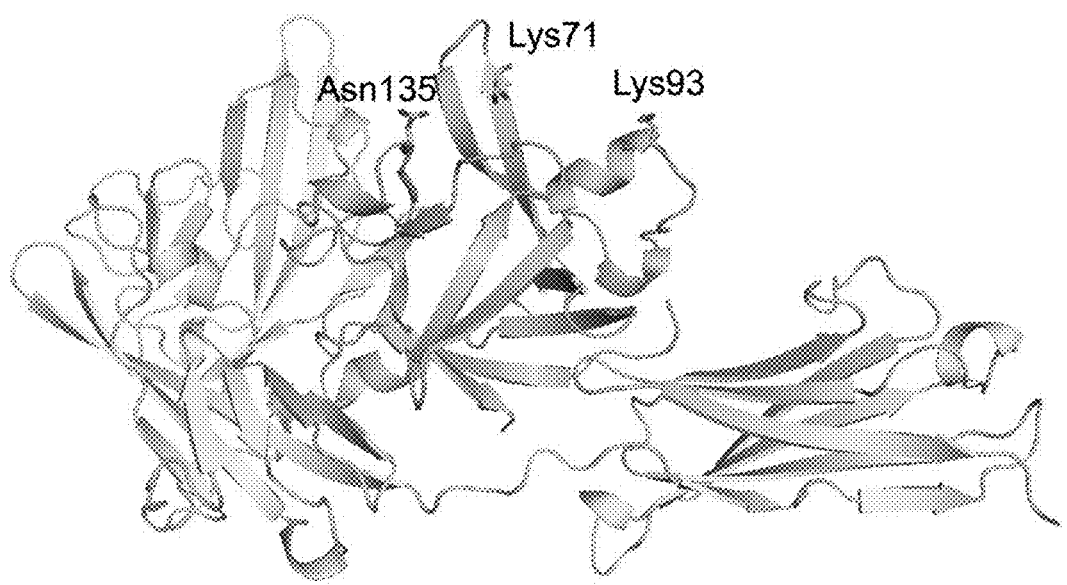
FIG. 3 shows complex of the interleukin-1 receptor (IL-1R) with the interleukin-1 receptor antagonist (IL-1RA). The sites for substitution with 1 and 2 (see FIG. 1) are shown.

Since many PylRS mutants have broad substrate specificity, we first screened only a small library of 22 previously evolved PylRS mutants for their ability to incorporate 1 and 2 into green fluorescence protein (GFP) in *E. coli*. The screening was based on the suppression of an amber nonsense codon at a permissive site in a GFP-encoding gene. Briefly, a plasmid, pLei-GFP$_{UV}$-N149UAG, which contains GFP$_{UV}$-149UAG and a copy of a tRNA$_{CUA}^{Pyl}$, was co-transformed into *E. coli* GeneHogs strain with a plasmid containing a variant of PylRS mutant. Protein expression was carried out in control LB medium and in medium supplemented with 1 mM 1 or 2. After induction of GFP expression and cultivation (12 h), cells were collected, washed, and analyzed using a fluorescence plate reader. (Incorporation efficiency scales with fluorescence.) As shown in FIG. 2, fluorescence analysis of *E. coli* cultures showed that significantly more full-length GFP$_{UV}$ proteins were produced in the presence of 1 or 2 for the best hit from the library. The fact that a small preliminary screen identified a mutant capable of incorporating 1 into GFP efficiently (20 mg/L vs. 80-120 mg/L for wt) indicates that further PylRS optimization is highly likely to produce an efficient expression system for proteins that incorporate (p-iodophenyl)alkanoyl nnAAs.

Example 3: Evolution and Optimization of Pyrrolysyl-tRNA Synthetase and its Cognate $tRNA_{CUA}^{Pyl}$ to Encode Homologous Non-Natural Amino Acids Derived from (Nε-(3-(4-Iodophenyl)propanoyl)lysine and Nε-(4-(4-Iodophenyl)butanoyl)lysine) into IL-1RA Mutants in *E. coli*

Figure 4:
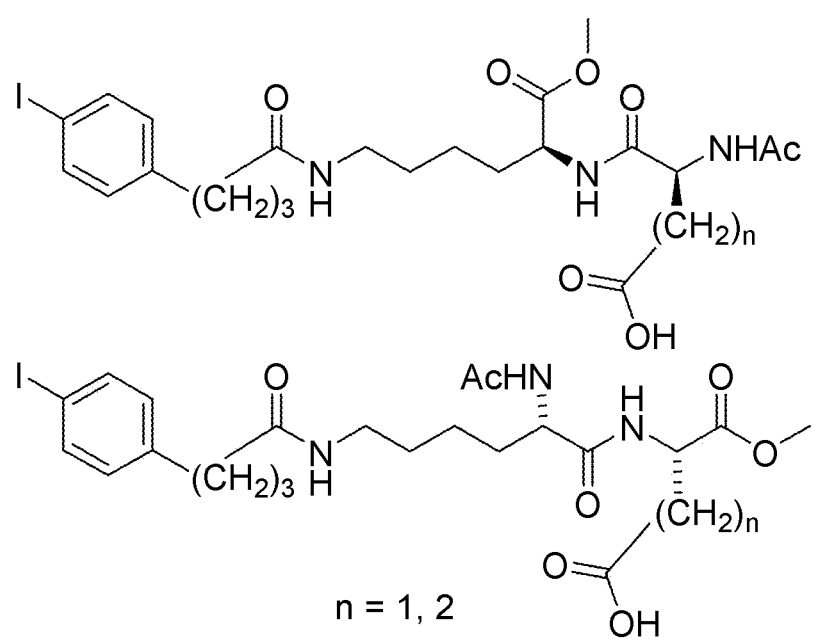
FIG. 4 shows dipeptide non-natural amino acids (nnAAs) for HPLC HSA binding assay studies (see Examples).
Figure 5:
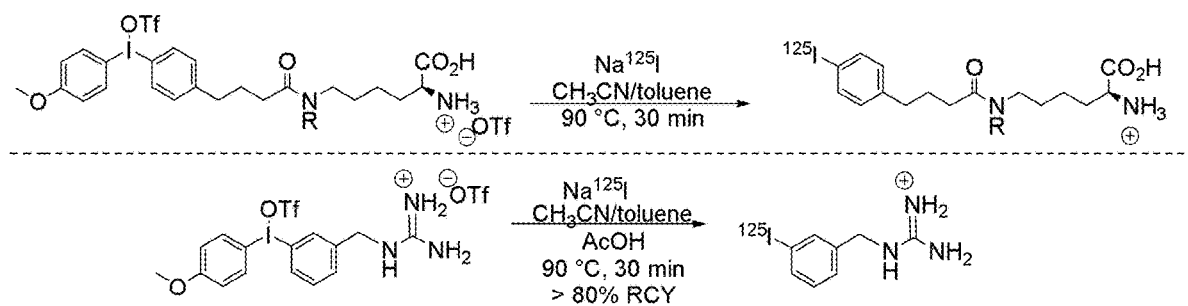
FIG. 5 shows a proposed one-step radioiodination route to radiolabeled nnAAs (top) based upon one-step synthesis of mIBG from a diaryliodonium salt precursor (bottom).

Three approaches are used to achieve efficient production of proteins incorporating the homologous nnAA pair (1 and 2).

Example 3A: Optimization of the Hit from the Initial Screen

The most promising hit from the initial screen (DizPKRs-Y349F, FIG. 2) serves as the basis for an additional mutant library, generated using error-prone PCR. A previously established selection system (Chen P R, et al. A Facile System for Encoding Unnatural Amino Acids in Mammalian Cells. *Angew Chem Int Ed.* 2009; 48, 4052-5) is used to identify PylRS mutants with increased activities. Briefly, the library is subjected to consecutive rounds of negative selection and positive selection using reporter genes containing an amber codon at a permissive position. The positive selection identifies functional PylRS mutants and is based on cells' resistance to chloramphenicol, which is conferred by the suppression of an amber mutation in the chloramphenicol acetyltransferase gene in the presence of the nnAA. The negative selection removes any PylRS mutants that can charge $tRNA_{CUA}^{Pyl}$ with endogenous amino acids; if $tRNA_{CUA}^{Pyl}$ is loaded with an endogenous amino acid, suppression of amber mutations in the toxic barnase gene leads to cell death. The negative selection is carried out in the absence of nnAAs. To determine the efficiency and fidelity of 1 and 2 incorporation by the evolved PylRS mutants in *E. coli*, we use the same fluorescence-based assay featured in our preliminary study (Example 2). In addition, the GFP protein is purified by affinity chromatography and analyzed by tandem mass spectrometry.

Example 3B: Identification of New Hits by De Novo Selection Using Several Large PylRS Mutant Libraries Since the hit we identified from the initial screening was optimized previously for incorporation of a different nnAA, it is unlikely to be the best PylRS variant for the incorporation of 1 and 2. Formal selection using a structure-guided, directed evolution approach is used. Based on the structure of PylRS (Nozawa K, et al. Pyrrolysyl-tRNA synthetase-tRNAPyl structure reveals the molecular basis of orthogonality. *Nature.* 2009; 457, 1163-7; Kavran J M, et al. Structure of pyrrolysyl-tRNA synthetase, an archaeal enzyme for genetic code innovation. *Proceedings of the National Academy of Sciences.* 2007; 104, 11268-73) and molecular modeling, we have constructed several PylRS mutant libraries in which residues within the amino acid binding pocket of PylRS were randomized. Among these libraries, three of them are derived from *Methanosarcina maize* PylRS (Library 1: L305, Y306, L309, N346, and C348; Library 2: L305, Y306, L309, C348, and V401; Library 3: L305, Y306, L309, C348, and Y384) and three of them are derived from *Methanosarcina barkeri* PylRS (Library 1: M241, A267, L270, Y271, and L274; Library 2: M265, L266, A267, C346, and M347; Library 3: L270, Y271, L274, V313, and V401). Our established standard selection process is applied.

Example 3C: tRNA Engineering to Improve Incorporation Efficiency of 1 and 2

The suppressor $tRNA_{CUA}^{Pyl}$ derived from archaea is a critical element in amber nonsense suppression; it is engineered to accommodate *E. coli* translational machinery. We focus on the T-stem and the portion of the A-stem of tRNA that interact with EF-Tu. Previously, we showed that the optimization of interaction between archaea *Methanococcus jannaschii* tRNA and *E. coli* EF-Tu led to up to 25-fold increase in amber suppression efficiency in *E. coli* (Guo J, et al. Evolution of Amber Suppressor tRNAs for Efficient Bacterial Production of Proteins Containing Nonnatural Amino Acids. *Angew Chem Int Ed.* 2009; 48, 9148-51). It is likely that a similar tRNA engineering strategy would lead to improved amber suppression efficiency of the PylRS-$tRNA_{CUA}^{Pyl}$ pair in *E. coli*. We construct tRNA libraries in which the nucleotides in the T-stem and A-stem is completely randomized. The nucleotides that form Watson-Crick base pairing with the above nucleotides is randomized as well. To identify tRNA mutants with higher suppression efficiency, our previously established selection system is used. The $tRNA_{CUA}^{Pyl}$ mutants that can survive in the presence of the highest concentration of chloramphenicol is selected for further evaluation using our GFP expression test (Guo J., et al, supra).

By means of the three complementary approaches outlined above, we obtain PylRS-$tRNA_{CUA}^{Pyl}$ pairs that display desirable incorporation efficiencies for 1 and 2.

Example 4: Synthesis of IL-1RA with 1 and 2

Based on the structure of interleukin-1 receptor (IL-1R) and the interleukin-1 receptor antagonist (IL-1RA) complex (Schreuder H, et al. A new cytokine-receptor binding mode revealed by the crystal structure of the IL-1 receptor with an antagonist. *Nature.* 1997; 386, 194-200), three residues at permissive sites of IL-1RA were selected for substitution with 1 and 2. Two of the permissive sites are lysine residues and the other one is an asparagine residue. All three are located on the surface of IL-1RA and do not interfere with its binding to IL-1R (FIG. 3). The control and mutant proteins are expressed in *E. coli* in the presence of the evolved PylRS-$tRNA_{CUA}^{Pyl}$ pair and the non-natural amino acid of interest (1 or 2), and purified as 6×His-tagged proteins by affinity chromatography. The 6×His-tag is removed by protease digestion subsequently, if necessary. The purity of the proteins is assessed by SDS-PAGE and the sequence is confirmed by MS-MS.

Example 5: Incorporation of Protein Surface Carboxylates into IL-1Ra Mutants and Assessment of Impact of Such Substitutions on In Vitro Binding of Tagged IL-1RA Mutants to Human Serum Albumin and IL-1R Our preliminary albumin binding results with 1 and its corresponding methyl ester demonstrated the carboxylate group provided an increase in albumin affinity. In their initial report, Dumelin and coworkers suggested that the free carboxylate of 1 (D- or L-isomer) mimicked the 5'-phosphate found in the DNA encoded library screen to enhance albumin affinity (Dumelin C E, et al. A portable albumin binder from a DNA-encoded chemical library. *Angew Chem, Int Ed.* 2008; 47, 3196-201). Intriguingly, they found that the anionic group needed to be six or more carbon atoms removed from the amide bond of the tag to achieve strong albumin targeting. Given the rather severe structural constraints of the aminoacyl-t-RNA synthetases (AARS) used to introduce nnAAs, it was thought far easier to introduce negatively charged amino acids near the site of tag insertion using standard site-directed mutagenesis, rather than attempt to evolve an AARS to accept a branched, negatively charged nnAA. To test the feasibility of the "encoded charge" approach to enhanced albumin targeting, we prepare the four dipeptides of 1 with Glu and Asp (FIG. 4), and assess their albumin affinity using a chromatographic binding assay described earlier (Hage D S, Austin J. High-performance affinity chromatography and immobilized serum albumin as probes for drug- and hormone-protein binding. *J Chromatogr B Biomed Sci Appl.* 2000; 739, 39-54). The data from these studies allow us to determine if albumin binding is sensitive to the position and identity of the negatively-charged carboxylate group; these data are used to inform and interpret the consequence of introducing a second mutant residue (Glu or Asp) in the vicinity of the albumin-targeting tag in IL-1RA.

Contemporaneously with these chemical synthesis studies, we also construct a small IL-1RA mutant library in which the two positions on either side of nnAA 1 are randomized. A subsequent chromatographic HSA binding assay contrasting these compounds with "control" 1-tagged IL-1RA mutants and wt IL-1RA is used to determine the generality and effectiveness of a protein surface charge in enhancing HSA affinity. Once the three best IL-1RA double mutants (one each selected from IL-1RA-Lys71-1, IL-1RA-Lys93-1, and IL-1RA-Asn135-1, positions referring to those of SEQ ID NO:1) are identified, these proteins and their 2-labeled homologs can be produced in quantity and subjected to detailed protein receptor studies. If a second mutation is indeed necessary for effective albumin binding, the perturbation introduced into the protein structure (2 amino acids instead of one) is still quite small.

Example 6: HSA Affinity Determination by Surface Plasmon Resonance

The binding affinities between IL-1RA and IL-1RA mutants and albumin are obtained using a BIAcore 2000 (BIAcore Inc., Piscataway, N.J.) using a modified procedure of Lacy (Lacy S E, et al. Generation and characterization of ABT-981, a dual variable domain immunoglobulin (DVD-Ig™) molecule that specifically and potently neutralizes both IL-1α and IL-1β. *MAbs.* 2015; 7, 605-19). Human and mouse albumin is captured on a CM5 chip using amine coupling at 5000 resonance units. IL-1RA and IL-1RA-mutants at 0, 0.625, 1.25, 2.5, 5, and 10 μm is injected at a flow rate of 20 μl/min for 30 s. The bound peptides are allowed to dissociate for 5 min before matrix regeneration using 10 mm glycine, pH 3. The signal from an injection passing over an uncoupled cell is subtracted from that of an immobilized cell to generate sensorgrams of the amount of peptide bound as a function of time. The running buffer, PBS containing 0.05% Tween 20, is used for all sample dilutions. BIAcore kinetic evaluation software (version 3.1) is used to determine $K_D$ from the association and dissociation rates using a one-to-one binding model.

Example 7: HSA Affinity Determination Direct Binding Assay

Albumin binding of radiolabeled IL-1RA and IL-1RA mutants (see below for the synthesis of the mutant proteins) is assessed using a modification to a procedure previously described by Nguyen (Nguyen A, et al. The pharmacokinetics of an albumin-binding Fab (AB.Fab) can be modulated as a function of affinity for albumin. *Protein Eng Des Sel.* 2006; 19, 291-7). Briefly, mouse and human albumin (Sigma; St. Louis, Mo.) are immobilized onto NUNC Maxisorp® 96-well plates at 2 mg/ml overnight at 4° C. The plates are blocked with binding buffer (PBS, 0.5% ovalbumin and 0.05% Tween-20) for 1 h at 25° C. IL-1RA mutants are serially diluted in binding buffer and added at 100 μl per well to the immobilized albumin for 30 m at 25° C. Unbound IL-1RA mutants are removed by washing wells with 0.05% PBS/Tween-20 and bound IL-1RA mutants are detected using a radioactivity plate reader. Alternatively, radiolabeled IL-1RA and IL-1RA mutants are assessed for albumin binding using ultrafiltration as described by Mueller (Muller C, et al. DOTA conjugate with an albumin-binding entity enables the first folic acid-targeted $^{177}$Lu-radionuclide tumor therapy in mice. *J Nucl Med.* 2013; 54, 124-31).

Example 8: Receptor Binding Studies with IL-1RA and IL-1RA Mutants

Affinity measurements are performed using IL-1R expressing cells (Steinkasserer A, et al. Human interleukin-1 receptor antagonist. High yield expression in *E. coli* and examination of cysteine residues. *FEBS Lett.* 1992; 310, 63-5; van der Laken C J, et al. Different behavior of radioiodinated human recombinant interleukin-1 and its receptor antagonist in an animal model of infection. *Eur J Nucl Med.* 1996; 23, 1531-5). The mouse helper T lymphocyte cell line D10.G4.1 (ATCC; Manassas, Va.) or EL-4-6.1 (Ludwig Institute for Cancer Research, Switzerland) cells are suspended at $10^7$ cells/ml in binding medium (RPMI 1640, 5% FCS, 20 mM HEPES pH 7.2), and 50 μl of cell suspension was added to each well of a 96-well filtration plate (Millipore). To each well 50 microliters of $^{125}$I-IL-1RA mutants at a final concentration of 50 pM is added. Unlabeled human IL-1RA (IL-1RA and IL-1RA mutants prepared in this work) are serially diluted in binding medium, and 50 μl aliquots of unlabeled ligand are added to each well. Receptor binding is allowed to proceed to equilibrium at 4° C. The plates are washed in binding medium by vacuum filtration, and the filters subsequently counted for bound radioactivity. Statistical analysis is performed using the one-way analysis of variance (ANOVA).

Example 9: Preparation for Analyzing by SPECT and Classical Methods the Biodistributions of $^{125}$I-Labeled Albumin Targeted and Control IL-1RA Proteins in Normal Mice A more direct, one-step approach to simplify the purification and isolation of $^{125}$I-radiolabeled products is explored (FIG. 5). Given that this approach has been successfully applied to the synthesis of a similarly protonated amine under acidic conditions ($^{125}$I-mIBG), no difficulties with the second route are anticipated.

These radio-iodinated amino acids are used in the first ever protein bacterial biosynthesis of radio-iodinated proteins for imaging. The drive to improve the efficiency of mutant IL-1RA protein production can be understood after consideration of the expected $^{125}$I-labeled IL-1RA protein yields. Table 2 shows the amount of labeled protein activity expected (per mL of medium) for no-carrier-added $^{125}$I-labeled 2 at different concentrations. While a 1% yield of protein from nnAAs is routinely obtained and is sufficient for mouse bio-distribution and imaging studies (50 µCi of IL-1RA from 5 mCi of nnAA), we have set a benchmark of >5% incorporation to reduce the amount of activity that needs to be handled and to reduce the impact of any radiolysis upon the bacterial cultures. Given the relatively small amounts of radioactivity used here and the low energy gamma emission of $^{125}$I (35.5 keV), it seems unlikely that radiolysis is a problem.

TABLE 2

Amount of labeled protein activity expected for no-carrier-added $^{125}$I-labeled 2 at different concentrations

| nnAA Concentration | nnAA Activity (mCi/ml) | | Protein Activity (µCi/ml) |
|---|---|---|---|
| | | Yield @ 40 mg/liter | |
| 1 mM | 2.125 | 0.23% | 4.8875 |
| 0.5 mM | 1.0625 | 0.46% | 4.8875 |
| 0.1 mM | 0.2125 | 2.30% | 4.8875 |
| 0.05 mM | 0.10625 | 4.60% | 4.8875 |
| | | Yield @ 100 mg/liter | |
| 1 mM | 2.125 | 0.58% | 12.21875 |
| 0.5 mM | 1.0625 | 1.15% | 12.21875 |
| 0.1 mM | 0.2125 | 5.75% | 12.21875 |
| 0.05 mM | 0.10625 | 11.50% | 12.21875 |

Example 10: Imaging and Biodistribution Studies

Tissue distribution in wild type BALB/C mice is performed for $^{125}$I-labeled IL-1RA (native) and two IL-1RA mutants labeled with 1 and two mutants labeled with 2 that demonstrate the highest IL-1R binding affinities. Tissue uptake is analyzed after administering, via the tail vein, a bolus injection of 10 µCi/mouse in a constant volume of 0.05 mL. Groups of 5 animals are euthanized by asphyxiation with carbon dioxide at 1, 4, 12, 24, 72 and 96 hours post injection. Tissues (tumor, blood, heart, liver, lungs, spleen, large and small intestine, stomach, kidneys, skeletal muscle, bone, adipose, testes, brain and tumor) are dissected, excised, weighed wet, transferred to plastic tubes and counted in an automated γ-counter. Tissue time-radioactivity levels are expressed as % injected dose per gram tissue (% ID/g) and % injected dose per organ (% DPO).

Imaging studies are performed for $^{125}$I-labeled IL-1RA (native) and the IL-1RA mutant tagged with 1 that shows the greatest blood retention as determined by the biodistribution studies above. The same mutant tagged with 2 serves as a second control. Imaging studies are carried out using the Inveon Trimodality imaging system (Siemens; Deerfield, Ill.) in microSPECT mode. Animals are injected with 50 µCi/mouse of labeled IL-1RA (wt or mutant). Groups of 3 animals are injected per compound studied and imaging takes place at 1, 24, 72 and 96 h post injection. After the last time point, animals are euthanized by asphyxiation with carbon dioxide. Tissues (tumor, blood, heart, liver, lungs, spleen, large and small intestine, stomach, kidneys, skeletal muscle, bone, adipose, testes, brain and tumor) are dissected, excised, weighed wet, transferred to plastic tubes and counted in an automated γ-counter. Tissue time-radioactivity levels are expressed as % injected dose per gram tissue (% ID/g) and % injected dose per organ (% DPO).

Example 11: Synthesis of Phenylpropanoic Acid Succinimidyl Ester Diaryliodonium Salt (6)

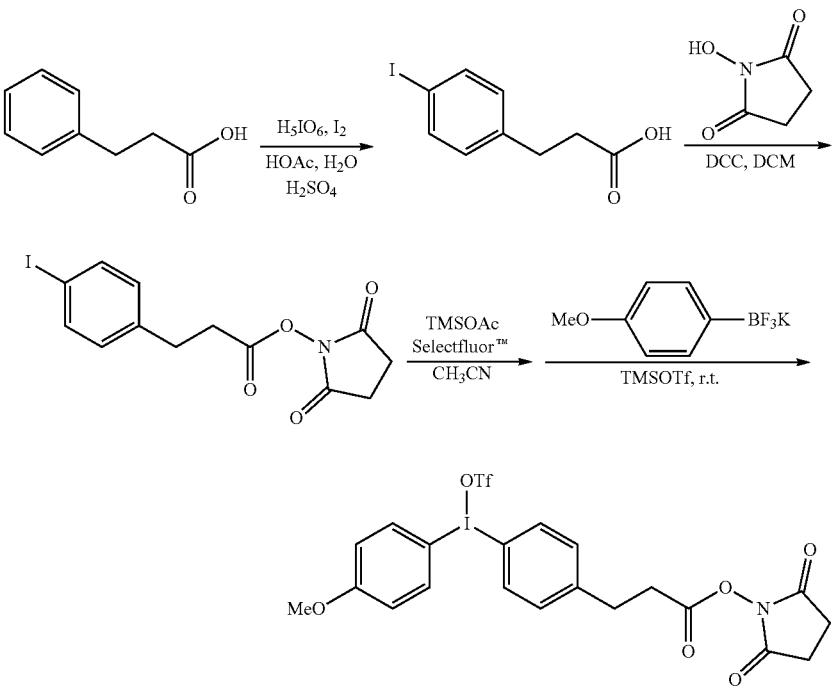

(1) 3-(4'-Iodophenyl)propanoic acid

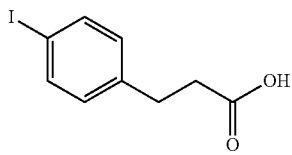 [SMILES: O=C(O)CCc1ccc(I)cc1]

A mixture of 3-phenylpropanoic acid (6.00 g, 40.0 mmol), $H_5IO_6$ (2.00 g, 8.60 mmol), iodine (4.06 g, 16.0 mmol) and 98% $H_2SO_4$ (1.2 mL) in water (8 mL) and acetic acid (40 mL) was heated at 67° C. for 17 h. The reaction mixture was cooled and quenched with water (100 mL). The crude product was then filtered, washed with water and hexane. The pure product (6.2 g, 56%) was obtained by recrystallization from toluene. White solid. $^1$H NMR (400 MHz, $CDCl_3$) δ 7.62 (d, J=8.4 Hz, 2H), 6.97 (d, J=8.0 Hz, 2H), 2.91 (t, J=7.6 Hz, 2H), 2.67 (t, J=7.6 Hz, 2H).

(2) 3-(4-Iodophenyl)propanoic acid succinimidyl ester

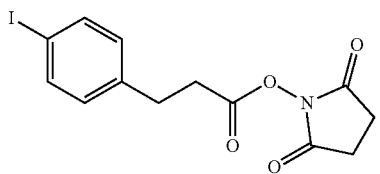 [SMILES: O=C(CCc1ccc(I)cc1)ON1C(=O)CCC1=O]

3-(4'-Iodophenyl)propanoic acid (10 mmol, 2.76 g, 1.0 eq.) and N-hydroxysuccinimide (15 mmol, 1.73 g, 1.5 eq) were dissolved in anhydrous $CH_2Cl_2$ (40 mL). The mixture was cooled to 0° C., and N,N'-dicyclohexylcarbodiimide (DCC, 15 mmol, 3.09 g, 1.5 eq) dissolved in 20 mL $CH_2Cl_2$ was added drop-wise slowly. The mixture was stirred overnight at room temperature. The N,N'-dicyclohexylurea was filtered out, the residue was washed with $CH_2Cl_2$, and the filtrate was evaporated to dryness purified by column chromatography and recrystallization with iso-propanol or toluene/hexane to afford succinimide as white solid (3.50 g, 94%). $^1$HNMR (400 MHz, $CD_3CN$) δ 7.66 (d, J=8.4 Hz, 2H), 7.08 (d, J=8.4 Hz, 2H), 2.95 ($A_2B_2$, t, 4H), 2.75 (s, 4H). $^{13}$CNMR (100 MHz, $CD_3CN$) δ 168.4, 166.7, 138.1, 135.9, 129.2, 89.5, 30.1, 27.8, 23.8; HRMS (ESI) Calcd for $C_{13}H_{12}NO_4INa$ (M+Na)+: 395.9709; Found: 395.9706.

(3) [4-(3-((2,5-dioxopyrrolidin-1-yl)oxy)-3-oxopropyl)phenyl]-(4'-methoxyphenyl)iodonium triflate (6)

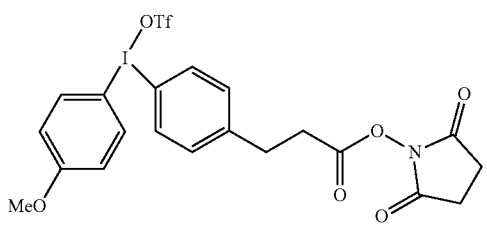 [SMILES: COc1ccc(I(OS(=O)(=O)C(F)(F)F)c2ccc(CCC(=O)ON3C(=O)CCC3=O)cc2)cc1]

In a $N_2$ charged glovebox, a solution of TMSOAc (13.0 mmol, 1.72 g, 2.6 eq.) in 20 mL dry $CH_3CN$ was added drop-wise to a solution of Selectfluor™ (6.5 mmol, 2.30 g, 1.3 eq.) in 20 mL dry $CH_3CN$. The resulting colorless mixture was then added drop-wise to a solution of (5.0 mmol, 1.87 g, 1.0 eq.) of 3-(4-Iodophenyl)propanoic acid succinimidyl ester in 20 mL dry $CD_3CN$. After being stirred at room temperature for 17 h, trifluoroborate salt (1.07 g, 5 mmol, 1.0 equiv.) was added to the solution followed by a solution of TMSOTf (1.00 g, 4.5 mmol, 0.9 eq.) in 20.0 mL of dry $CH_3CN$ was added drop-wise and the mixture was allowed to stand at room temperature for 30 min. After the solvent acetonitrile was removed, 100 mL of deionized water was added and the mixture was extracted (30 mL×3) with $CH_2CH_2$. The combined organic layers were washed with water (50 mL×1) and the obtained water layers were extracted (50 mL×2) with $CH_2CH_2$ again. The combined organic extracts were dried over sodium sulfate, filtered, and the solvent was removed by rotary evaporation. The residue was dissolved in 1.0 mL $CH_3CN$ and added drop-wise to 200 mL of MTBE to precipitate the diaryliodonium triflate product. This solid was dissolved in 1 mL acetonitrile/water (9:1 by volume) solution and slowly passed down an Amberlite IRA-400 ion exchange column (triflate counter ion). After removal of the solvents under reduced pressure, the purified iodonium triflate product (2.49 g, 79%) of was obtained as a colorless solid. $^1$H NMR (400 MHz, $CD_3CN$) δ 8.01 (d, J=9.2 Hz, 2H), 7.98 (d, J=8.4 Hz, 2H), 7.44 (d, J=8.4 Hz, 2H), 7.05 (d, J=9.2 Hz, 2H), 3.84 (s, 3H), 3.07 (t, J=6.8 Hz, 2H), 2.97 (t, J=6.8 Hz, 2H), 2.74 (s, 4H); $^{13}$C NMR (75 MHz, $CD_3CN$) δ 170.0, 168.2, 163.3, 145.4, 137.6, 135.1, 132.5, 118.1, 111.6, 101.6, 55.7, 31.3, 29.5, 25.4; $^{19}$F NMR ($CD_3CN$, 282 MHz): d −79.2 (s, 3 F). HRMS (ESI) Calcd for $C_{20}H_{19}NO_5I$ (M-OTf)+: 480.0308; Found: 480.0310.

Example 12: Radioiodination of Compound (6)

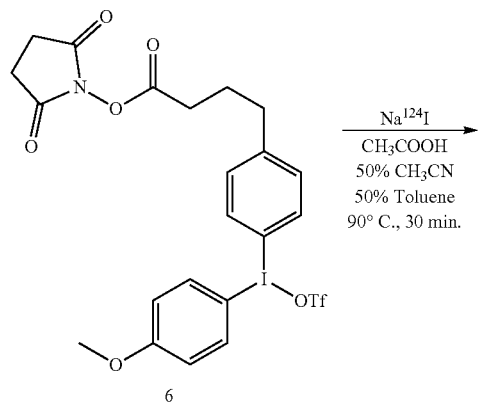

an acidic, slightly buffered solution. The initial activity was recorded for later calculations. Because the volume of water was so small, initial drying of the Na$^{124}$I solution was not required.

5 mg of the diaryliodonium precursor [4-(3-((2,5-dioxopyrrolidin-1-yl)oxy)-3-oxopropyl)phenyl]-(4'-methoxyphenyl)iodonium triflate was dissolved in 400 µL of CH$_3$CN. The mixture was allowed to stand for 10 minutes to make certain all of the crystalline compound had dissolved. The diaryliodonium precursor was added to the first reaction vial and then the solution was evaporated with a stream of dry argon at 90° C. After the solvent was removed completely, 125 µL of CH$_3$CN was added (with shaking or stirring) to dissolve the salts. Toluene (125 µL) was added and the solution was heated at 90° C. for 30 minutes. Silica TLC (100% ethyl acetate) was performed to determine the labeling efficiency. The reaction mixture was purified by passing it through a silica sep-pak and the crude product was purified by reverse phase HPLC to afford the desired product in 94% yield.

Example 13: Synthesis of Thioamide Compound

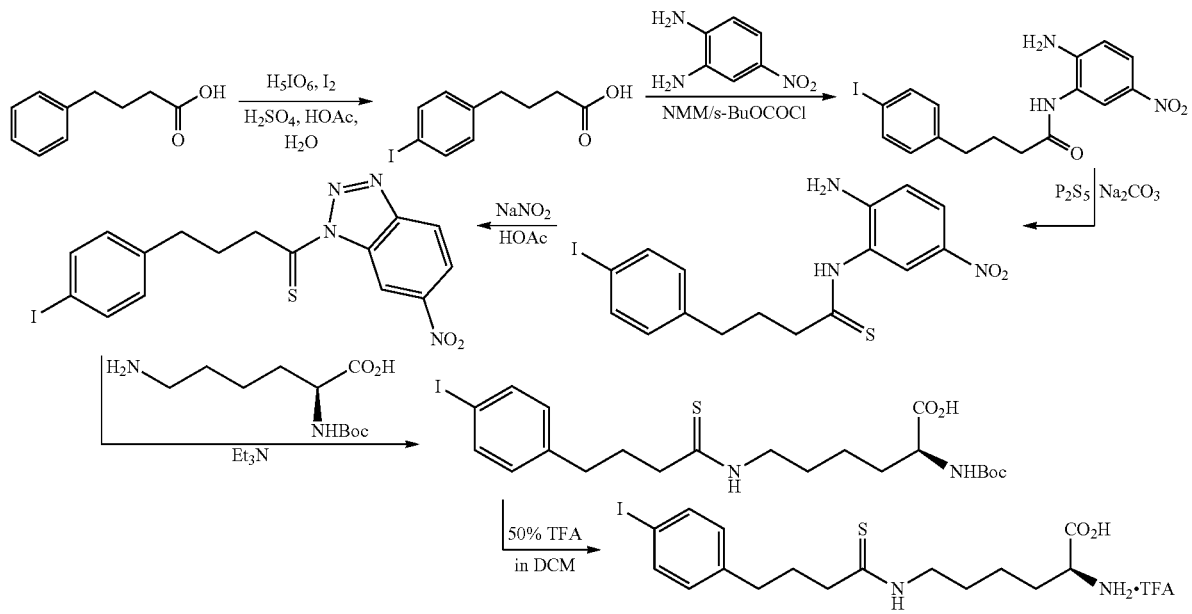

-continued

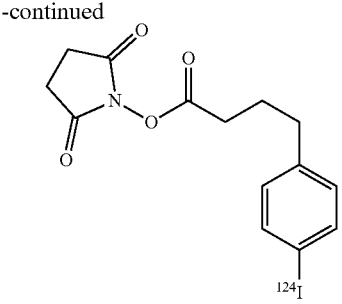

94%, n = 2
7

Aqueous Na$^{124}$I was dissolved in 0.1M NaOH. 1 µL of the Na$^{124}$I solution (approximately 1 mCi) was added to a first reaction vial along with 1 µL of 1.0 M AcOH to afford (1) 4-(4'-Iodophenyl)butanoic acid A mixture of 4-phenylbutanoic acid (20.0 g, 121.8 mmol), H$_5$IO$_6$ (5.56 g, 24.4 mmol), iodine (13.30 g, 52.4 mmol), 10 M H$_2$SO$_4$ (5.0 mL), water (36 mL) and acetic acid (166 mL) was heated at 70° C. for 19 h. The reaction mixture was cooled and evaporated to dryness. The residue was dissolved in EtOAc (300 mL) and washed with aqueous Na$_2$S$_2$O$_3$ (2×200 mL), brine (2×200 mL), dried over Na$_2$SO$_4$, filtered, and evaporated to leave a yellow solid. The crude product was precipitated from EtOAc/hexane at 0° C. to afford product as light yellow solid (15.0 g, 42%). $^1$H NMR (400 MHz, CDCl$_3$) δ 11.0 (brs, 1H), 7.61 (d, J=8.4 Hz, 2H), 6.95 (d, J=8.0 Hz, 2H), 2.63 (t, J=7.6 Hz, 2H), 2.38 (t, J=7.6 Hz, 2H).

(2) N-(2-amino-5-nitrophenyl)-4-(4-iodophenyl) butanamide

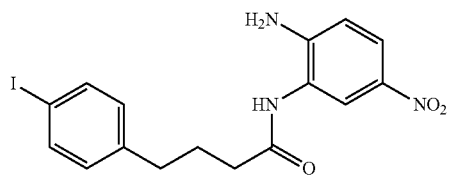 [SMILES: Nc1ccc([N+](=O)[O-])cc1NC(=O)CCCc1ccc(I)cc1]

4-(4'-Iodophenyl)butanoic acid (11.60 g, 40 mmol) was dissolved in THF (200 mL), and N-methylmorpholine (NMM) (8.8 mL, 80 mmol, 2.0 equiv) was added at −20° C. under N$_2$. Isobutyl chloroformate (5.2 mL, 40 mmol, 1.0 equiv) was added dropwise and the reaction mixture was stirred for 30 min. A solution of 4-nitro-1,2-phenylenediamine (6.12 g, 40 mmol, 1.0 equiv) in THF (100 mL) was added, and the mixture stirred for a further 1.5 h at −20° C. and 15 h at 23° C. The precipitate was filtered off, and the filtrate was evaporated to dryness. The residue was dissolved in EtOAc (300 mL) and washed with aqueous solutions of 1 M NaH$_2$PO$_4$ (2×100 mL), saturated brine (2×100 mL), saturated NaHCO$_3$ (2×100 mL), and saturated NaCl (2×100 mL). The EtOAc solution was dried over Na$_2$SO$_4$, and evaporated to dryness. The crude product was sonicated in EtOAc until it solidified. The remaining solid was filtered and dried in vacuo to yield the titled compound (10.77 g, 63%) as a yellow-brown solid.

(3) N-(2-Amino-5-nitrophenyl)-4-(4-iodophenyl) butanethioamide

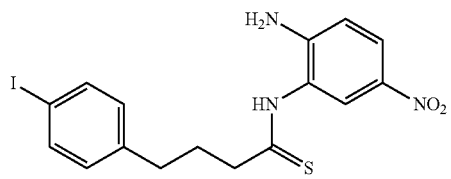 [SMILES: Nc1ccc([N+](=O)[O-])cc1NC(=S)CCCc1ccc(I)cc1]

P$_2$S$_5$ (4.44 g, 20 mmol, 1.0 equiv) was added to a suspension of Na$_2$CO$_3$ (1.08 g, 10 mmol, 0.5 equiv) in THF (200 mL) at 23° C. under a flow of N$_2$. After 1 h, the mixture was cooled to 0° C. and N-(2-amino-5-nitrophenyl)-4-(4-iodophenyl)butanamide (8.50 g, 20 mmol) in THF (100 mL) was added dropwise. The resulting mixture stirred for 2 h at 0° C. and for 1 h at 23° C. The solvent was evaporated and the residue was dissolved in EtOAc (200 mL), washed with 5% aqueous NaHCO$_3$ (2×100 mL). The organic phase was separated and the aqueous phase was extracted with EtOAc (100 mL). The combined organic phases were dried over Na$_2$SO$_4$, filtered and evaporated to dryness. The material was dissolved in EtOAc, sonicated, filtered, and dried in vacuo to yield the titled compound (6.89 g, 76%) as a yellow solid.

(4) 4-(4-Iodophenyl)-1-(6-nitro-1H-benzo[d][1,2,3] triazol-1-yl)butane-1-thione

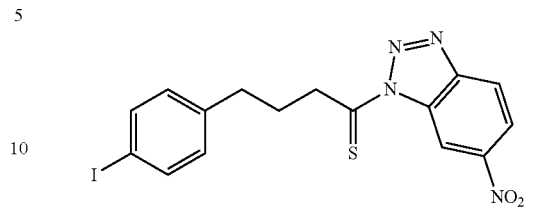

N-(2-Amino-5-nitrophenyl)-4-(4-iodophenyl)butanethioamide (5.68 g, 12.8 mmol) was dissolved in glacial acetic acid (diluted with 5% water, 300 mL) by gentle warming at 40° C. The solution was cooled to 0° C. and NaNO$_2$ (1.32 g, 19.2 mmol, 1.5 eq) was added in portions over 20 min with stirring. After 30 min, the precipitated product was filtered, washed with water and the filtrate was extracted with EtOAc (2×150 mL). The combined organic phases were washed successively with H$_2$O (3×100 mL), saturated NaHCO$_3$ (2×100 mL), and brine (2×100 mL), was dried, and then was evaporated to dryness. The obtained solid was sonicated in a small amount of EtOAc (5 mL). The EtOAc was decanted away and the remaining solid was filtered. The product (yellow solid, 3.23 g, 56%) was combined and dried in vacuo.

(5) N$^2$-(tert-butoxycarbonyl)-N$^6$-(4-(4-iodophenyl) butanethioyl)-L-lysine

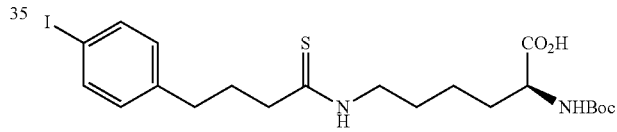

A cooled solution (0° C.) of the thioacylating reagent (N-(2-amino-5-nitrophenyl)-4-(4-iodophenyl)butanethioamide, 5 mmol, 2.26 g) in 75 mL of THF was treated, dropwise, with a solution of Boc-Lys-OH (5 mmol, 1.23 g) and triethylamine in 15 mL of THF and 3.0 mL of H$_2$O over the course of 1 h. After the addition was complete, the mixture was allowed to stir overnight at room temperature. The mixture was extracted with EtOAc, and the organic layer was dried over Na$_2$SO$_4$, and evaporated. The residue was purified by silica gel flash chromatography (hexane/EtOAc, 1/1, followed by MeOH) to afford the title compound (1.18 g) in 44% yield.

(6) N$^6$-(4-(4-iodophenyl)butanethioyl)-L-lysine, trifluoroacetate salt

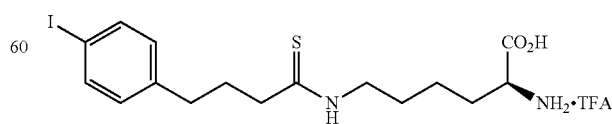

Trifluoroacetic acid (2.0 mL) was added to a solution of N$^2$-(tert-butoxycarbonyl)-N$^6$-(4-(4-iodophenyl)butanethioyl)-L-lysine (1.05 g, 2 mmol) in dry DCM (2 mL), and the reaction mixture was allowed to stir for 4 h at room temperature. The solvents were evaporated under reduced pressure, and dried under vacuum overnight. The residue was dissolved ethyl acetate (10.0 mL) and the solution was allowed to stand undisturbed for 12 h. The precipitated was filtered and dried in vacuum to give the titled modified lysine derivative (0.97 g, 91%) as an off-white solid.

Those skilled in the art will recognize, or be able to ascertain using no more than routine experimentation, many equivalents to the specific embodiments of the invention described herein. Where any concept(s) or element(s) of the invention is separately presented for convenience, it is understood that the combination of any such separately presented concept(s) or element(s), as necessary, is also encompassed by the invention. Such equivalents are intended to be encompassed by the claims.

The contents of the patents and references cited throughout this specification are hereby incorporated by reference in their entireties.

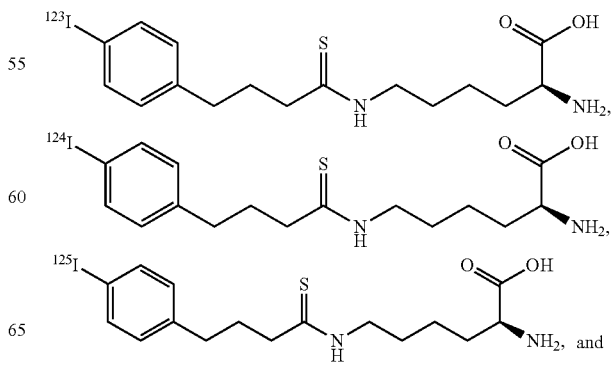

-continued
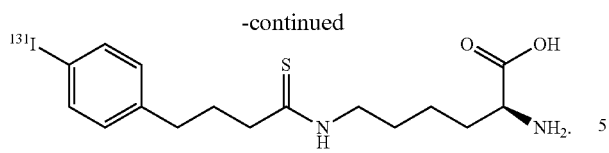

We claim:

1. A method of substituting a natural amino acid in a first polypeptide with a non-natural amino acid to obtain a modified polypeptide, wherein the non-natural amino acid comprises a moiety selected from the group consisting of: an albumin-targeting group and a radiolabelled albumin-targeting group, comprising:
   (a) selecting at least one amino acid residue in the first polypeptide to be substituted with the non-natural amino acid;
   (b) selecting a polynucleotide encoding the first polypeptide;
   (c) modifying the polynucleotide such that the amino acid residue to be substituted is encoded by a nonsense codon;
   (d) expressing the modified polynucleotide in a cell, wherein the cell is in the presence of the non-natural amino acid and expresses a suppressor tRNA and its cognate tRNA synthetase wherein the suppressor tRNA recognizes the nonsense codon of step (c), and the cell incorporates the non-natural amino acid into the modified polypeptide at the nonsense codon of step (c) during translation,
   wherein the albumin-targeting group or radiolabelled albumin-targeting group is selected from the group consisting of:

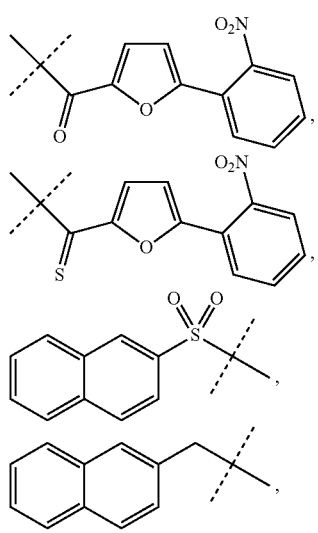

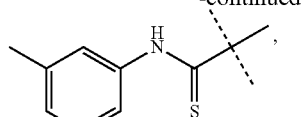

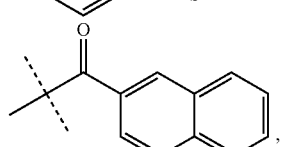

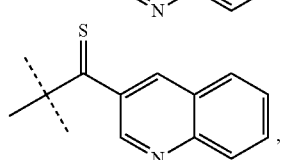

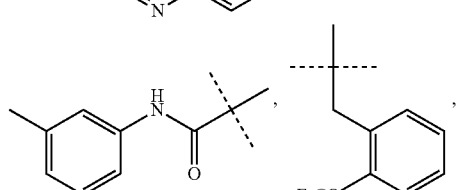

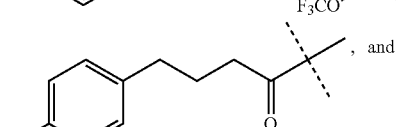

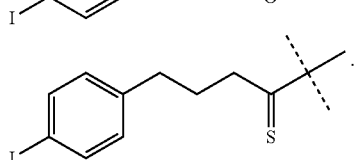

2. The method of claim 1, wherein the non-natural amino acid is Nε-(4-(4-iodophenyl)butanoyl)lysine, or a pharmaceutically acceptable salt thereof.

3. The method of claim 1, wherein the non-natural amino acid is Nε-(4-(4-iodophenyl)butanethioyl) lysine, or a pharmaceutically acceptable salt thereof.

4. The method of claim 1, further comprising step (e), purifying the modified polypeptide.

5. The method of claim 1, wherein the radiolabel is $^{123}$I, $^{124}$I, $^{125}$I, or $^{131}$I.

6. The method of claim 1, wherein the non-naturally occurring amino acid is selected from the group consisting of: